United States Patent
Chan

(10) Patent No.: US 10,238,656 B2
(45) Date of Patent: Mar. 26, 2019

(54) COMBINATION THERAPY FOR CANCER

(71) Applicant: Eli Lilly and Company, Indianapolis, IN (US)

(72) Inventor: Edward Michael Chan, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/115,995

(22) PCT Filed: Feb. 19, 2015

(86) PCT No.: PCT/US2015/016529
§ 371 (c)(1),
(2) Date: Aug. 2, 2016

(87) PCT Pub. No.: WO2015/130540
PCT Pub. Date: Sep. 3, 2015

(65) Prior Publication Data
US 2017/0173013 A1 Jun. 22, 2017

Related U.S. Application Data

(60) Provisional application No. 61/944,811, filed on Feb. 26, 2014.

(51) Int. Cl.
*A61K 39/395* (2006.01)
*A61K 31/506* (2006.01)
*C07K 16/28* (2006.01)
*A61K 39/00* (2006.01)

(52) U.S. Cl.
CPC .......... *A61K 31/506* (2013.01); *A61K 39/395* (2013.01); *A61K 39/39541* (2013.01); *C07K 16/2863* (2013.01); *A61K 2039/505* (2013.01); *C07K 2317/21* (2013.01); *C07K 2317/76* (2013.01)

(58) Field of Classification Search
None
See application file for complete search history.

(56) References Cited

U.S. PATENT DOCUMENTS

2003/0108545 A1 6/2003 Rockwell
2013/0203765 A1* 8/2013 Brain .................. C07D 487/04
514/252.16

FOREIGN PATENT DOCUMENTS

WO 03/075840 9/2003
WO 10/075074 7/2010

OTHER PUBLICATIONS

Krupitskaya Yelena, et al., Ramucirumab, a fully human mAb to the transmembrane signaling tyrosinekinase VEGFR-2 for the potential treatment of cancer, Current Opinion in Investigational Drugs, V. 10, i. 6 pp. 597-605 (2009) UK.

Patnaik, et al., "Efficacy and Safety of Abemaciclib, an Inhibitor of CDK4 and CDK6, for Patients with Breast Cancer, Non-Small Cell Lung Cancer, and Other Solid Tumors," Cancer Discovery, vol. 6, No. 7, pp. 1-14 (Jul. 2016).

Tate, et al., "Semi-Mechanistic Pharmacokinetic/Pharmacodynamic Modeling of the Antitumor Activity of LY2835219, a New Cyclin-Dependent Kinase 4/6 Inhibitor, in Mice Bearing Human Tumor Xenografts," Clinical Cancer Research, vol. 20, No. 14, pp. 1-12 (Jul. 15, 2014).

Tate, et al., "A Population Pharmacokinetic and Pharmacodynamic Analysis of Abemaciclib in a Phase I Clinical Trial in Cancer Patients," Clinical Pharmacokinetics, vol. 57, No. 3, pp. 335-344 (Mar. 2018).

Gelbert, et al., "Preclinical characterization of the CDK4/6 inhibitor LY2835219: in vivo cell cycle-dependent/independent anti-tumor activities alone/in combination with gemcitabine," Investigational New Drugs, vol. 32, No. 5, pp. 825-837 (Oct. 2014).

Franco, et al., "Targeted Anti-Vascular Endothelial Growth Factor Receptor-2 Therapy Leads to Short-term and Long-term Impairment of Vascular Function and Increase in Tumor Hypoxia," Cancer Research, vol. 66, No. 7; pp. 3639-3648 (2006).

Ellis, et al., "VEGF-targeted therapy: mechanisms of anti-tumour activity," Nature Reviews Cancer, vol. 8, pp. 579-591 (Jul. 3, 2008).

Skobe, et al., "Halting angiogenesis suppresses carcinoma cell invasion," Nature Medicine, vol. 3, No. 11, pp. 1222-1227 (Nov. 1997).

Prewett, et al., "Antivascular Endothelial Growth Factor Receptor (Fetal Liver Kinase 1) Monoclonal Antibody Inhibits Tumor Angiogenesis and Growth of Several Mouse and Human Tumors," Cancer Research, vol. 59, No. 20 (Oct. 1999).

Bruns, et al., "Vascular endothelial growth factoris an in vivo survival factor for tumor endothelium in a murine model of colorectal carcinoma liver metastases," Cancer, vol. 89, Issue 3, pp. 488-499 (Aug. 2000).

Shapiro, Geoffrey, et al., "A first-in-human phase I study of the CDK4/6 inhibitor LY2835219, for patients with advanced cancer," Journal of Clinical Oncology, vol. 31, No. 15 Suppl, p. 2500 (May 2013).

Spratlin, Jennifer L., et al., "Phase I Pharmacologic and Biologic Study of Ramucirumab (IMC-1121B), a Fully Human Immunoglobulin G1 Monoclonal Antibody Targeting the Vascular Endothelial Growth Factor Receptor-2," Journal of Clinical Oncology, vol. 28, No. 5, pp. 780-787 (Feb. 2010).

(Continued)

*Primary Examiner* — Sheela J. Huff
(74) *Attorney, Agent, or Firm* — Tina M Tucker

(57) ABSTRACT

The present invention provides preparation of medicaments for use in treating and methods of treating non-small cell lung cancer in a patient comprising: [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, in combination, as further described herein, with an anti-VEGFR2 antibody, preferably, ramucirumab.

6 Claims, No Drawings

Specification includes a Sequence Listing.

(56) References Cited

OTHER PUBLICATIONS

Garcia-Carbonero, Rocio, et al., "A phase II, open-label study evaluating the safety and efficacy of ramucirumab combined with mFOLFOX-6 as a first-line therapy in patients (pts) with metastatic colorectal cancer (mCRC)," Journal of Clinical Oncology, vol. 30, No. 4 Suppl, p. 533 (Feb. 2012).

Pinto, Ana Catarina, et al., (2011) "Combination Chemotherapy in Cancer: Principles, Evaluation and Drug Delivery Strategies," Current Cancer Treatment—Novel Beyond Conventional Approaches, Prof. Oner Ozdemir (Ed.), ISBN: 978-953-307-397-2, InTech. See p. 694.

Shaheen, RM, et al., "Inhibited Growth of Colon Cancer Carcinomatosis by Antibodies to Vascular Endothelial and Epidermal Growth Factor Receptors," British Journal of Cancer, vol. 85, No. 4, pp. 584-589 (2001).

* cited by examiner

COMBINATION THERAPY FOR CANCER

The present invention relates to a combination of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine with an anti-human VEGFR2 antibody, preferably ramucirumab, and to methods of using the combination to treat certain disorders, such as non-small cell lung cancer (NSCLC).

The present invention is in the field of treatment of NSCLC. Lung cancer ranks as one of the most common causes of death due to cancer in both men and women throughout the world. The two main types of lung cancer are small cell lung cancer and NSCLC. Non-small cell lung cancer makes up approximately 80% or more of lung cancer cases. Treatment can involve surgery, chemotherapy, or radiation therapy, as well as combinations of these treatments.

Unfortunately, a cure for NSCLC still remains elusive and there exists a need for more and different therapies that may prove to be effective in treating NSCLC.

[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine (abemaciclib) is an inhibitor of cyclin dependent kinases 4 and 6 (CDK4/6). Abemaciclib and methods of making and using this compound including for the treatment of cancer and more specifically for the treatment of NSCLC are disclosed in WO2010/075074. Furthermore, clinical activity for the compound has been observed in patients with NSCLC.

Ramucirumab is a fully human monoclonal antibody directed against the vascular endothelial growth factor receptor 2 (VEGFR2). Ramucirumab and methods of making and using this compound including for the treatment of neoplastic diseases such as solid and non-solid tumors are disclosed in WO2003/075840. Furthermore, clinical activity for ramucirumab has also been reported in patients with NSCLC (PRNewswire "Ramucirumab Improved Survival in Second-Line Study of Patients with Non-Small Cell Lung Cancer" (INDIANAPOLIS, Feb. 19, 2014)). On Dec. 16, 2014, ramucirumab (Cyramza®) was approved by the U.S. F.D.A. for treating NSCLC.

A novel combination of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine and ramucirumab is herein presented. Although combinations of CDK4/6 inhibitors and inhibitors of VEGFR2 have been contemplated in the art, the present inventor discloses herein methods of treating NSCLC by using a novel combination of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine and an anti-VEGFR2 Ab as part of a specific treatment regimen that provides enhanced and/or unexpected beneficial therapeutic effects from the combined activity of these therapeutic agents in some NSCLC patients as compared to the therapeutic effects provided by either agent alone. The present inventor also discloses herein methods of treating NSCLC by using a novel combination of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine and ramucirumab as part of a specific treatment regimen that provides enhanced and/or unexpected beneficial therapeutic effects from the combined activity of these therapeutic agents in some NSCLC patients as compared to the therapeutic effects provided by either agent alone.

Accordingly, the present invention provides a method of treating NSCLC in a patient, comprising administering to a NSCLC patient in need of such treatment an effective amount of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, in combination with an effective amount of an anti-VEGFR2 Ab. The present invention also provides a method of treating NSCLC in a patient, comprising administering to a NSCLC patient in need of such treatment an effective amount of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, in combination with ramucirumab. Optionally these methods further comprise the administration of an effective amount of one or more anti-tumor agents selected from the group consisting of pemetrexed, gemcitabine, docetaxel, bevacizumab, carboplatin and cisplatin. An effective amount of these anti-tumor agents is typically the dose stated on that agents label.

The invention further provides a pharmaceutical composition comprising [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, with one or more pharmaceutically acceptable carriers, diluents, or excipients, in combination with a pharmaceutical composition of an anti-VEGFR2 Ab with one or more pharmaceutically acceptable carriers, diluents, or excipients. The invention also provides a pharmaceutical composition comprising [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, with one or more pharmaceutically acceptable carriers, diluents, or excipients, in combination with a pharmaceutical composition of ramucirumab, with one or more pharmaceutically acceptable carriers, diluents, or excipients.

In addition, the invention provides a kit comprising [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, and an anti-VEGFR2 Ab. The invention also provides a kit comprising [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, and ramucirumab. The invention further provides a kit comprising a pharmaceutical composition comprising [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, with one or more pharmaceutically acceptable carriers, diluents, or excipients, and a pharmaceutical composition comprising an anti-VEGFR2 Ab, with one or more pharmaceutically acceptable carriers, diluents, or excipients. The invention also provides a kit comprising a pharmaceutical composition comprising [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, with one or more pharmaceutically acceptable carriers, diluents, or excipients, and a pharmaceutical composition comprising ramucirumab, with one or more pharmaceutically acceptable carriers, diluents, or excipients.

The invention further provides a combination comprising [5-(4-ethyl-piperazin-1-ylmethyl)-pyridin-2-yl]-[5-fluoro-4-(7-fluoro-3-isopropyl-2-methyl-3H-benzoimidazol-5-yl)- pyrimidin-2-yl]-amine or a pharmaceutically acceptable salt thereof and an anti-VEGFR2 Ab, for simultaneous, separate or sequential use in the treatment of NSCLC.

The invention further provides a combination comprising [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or a pharmaceutically acceptable salt thereof and ramucirumab, for simultaneous, separate or sequential use in the treatment of NSCLC.

The invention further provides the use of a combination of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, and an anti-VEGFR2 Ab in therapy. The invention further provides the use of a combination of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, and an anti-VEGFR2 Ab for the manufacture of a medicament for the treatment of NSCLC.

The invention further provides the use of a combination of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, and ramucirumab in therapy. The invention further provides the use of a combination of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, and ramucirumab for the manufacture of a medicament for the treatment of NSCLC.

Another aspect of the present invention is a method of treating non-small cell lung cancer in a patient, comprising administering to a non-small cell lung cancer patient in need of treatment:

a) ramucirumab at 10 mg/kg on day 1 of a 21-day cycle; and
b) [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, at 50-200 mg PO every 12 hours on days 1-21 of a 21-day cycle.

A further aspect of the present invention provides:

a) use of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, for the manufacture of a medicament for the treatment of NSCLC;
b) use of ramucirumab for the manufacture of a medicament for the treatment of NSCLC;

wherein ramucirumab is administered at 10 mg/kg IV on Day 1 of a 21-day cycle and [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, is administered at 50-200 mg PO every 12 hours on days 1-21 of a 21-day cycle.

As used herein, the compound's name "[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine" is disclosed in WO2010/075074 and refers to the compound with the following structure:

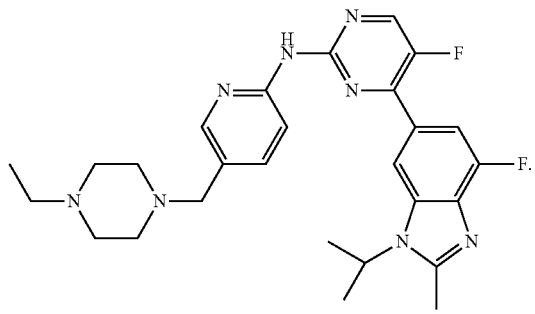 [SMILES: CCN1CCN(Cc2ccc(Nc3ncc(F)c(-c4cc(F)c5nc(C)n(C(C)C)c5c4)n3)nc2)CC1]

This compound's CAS registry number is 1231929-97-7. The generic name for the compound is abemaciclib. Alternative compound names include 2-pyrimidinamine, N-[5-[(4-ethyl-1-piperazinyl)methyl]-2-pyridinyl]-5-fluoro-4[4-fluoro-2-methyl-1-(1-methylethyl)-1H-benzimidazol-6-yl]-, 1-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, and N-(5-((4-ethylpiperazin-1-yl)methyl)pyridin-2-yl)-5-fluoro-4-(4-fluoro-1-isopropyl-2-methyl-1H-benzo[d]imidazole-6-yl)pyrimidin-2-amine.

As used herein, the term "VEGFR2" refers to the polypeptide whose amino acid sequence is that given in SEQ ID NO: 9. VEGFR2 is also known as KDR.

As used herein, the term "anti-VEGFR2 Ab" refers to an antibody comprising: a light chain variable region (LCVR) whose amino acid sequence is that given in SEQ ID NO: 2, and a heavy chain variable region (HCVR) whose amino acid sequence is that given in SEQ ID NO: 4, wherein that the anti-VEGFR2 Ab binds to VEGFR2 with sufficient affinity and specificity. In some embodiments, an anti-VEGFR2 Ab is an antibody comprising: a light chain whose amino acid sequence is that given in SEQ ID NO: 6, and a heavy chain whose amino acid sequence is that given in SEQ ID NO: 8 and that binds to VEGFR2 with sufficient affinity and specificity. In other embodiments of the present invention the anti-VEGFR2 Ab is ramucirumab. The antibody selected will have a sufficiently strong binding affinity for VEGFR2. For example, the antibody will generally bind VEGFR2 with a $K_d$ value of between about 100 nM-about 1 pM. Antibody affinities may be determined by a surface plasmon resonance based assay (such as the BIAcore assay is described in PCT Application Publication No. WO2005/012359); enzyme-linked immunoabsorbent assay (ELISA); and competition assays (e.g. a radiolabeled antigen binding assay (RIA)), for example. In one embodiment, Kd is measured by a RIA performed with an anti-VEGFR2 Ab, preferably ramucirumab.

As used herein, the term "ramucirumab" also known as Cyramza®, IMC-1121b, CAS registry number 947687-13-0, refers to an anti-VEGFR2 Ab comprising: two light chains, each of whose amino acid sequence is that given in SEQ ID NO: 6, and two heavy chains, each of whose amino acid sequence is that given in SEQ ID NO: 8.

Unless indicated otherwise, the term "antibody" refers to an immunoglobulin molecule comprising two heavy chains (HC) and two light chains (LC) interconnected by disulfide bonds. The amino terminal portion of each chain includes a variable region of about 100 to about 110 amino acids primarily responsible for antigen recognition via the complementarity determining regions (CDRs) contained therein. The carboxy-terminal portion of each chain defines a constant region primarily responsible for effector function.

As used herein, the term "antigen-binding fragment" refers to any antibody fragment that retains the ability to bind to its antigen. Such "antigen-binding fragments" can be selected from the group consisting of Fv, scFv, Fab, F(ab')$_2$, Fab', scFv-Fc fragments and diabodies. An antigen-binding fragment of an antibody will typically comprise at least one variable region. Preferably, an antigen-binding fragment comprises a heavy chain variable region (HCVR) and a light chain variable region (LCVR). More preferably, an antigen-binding fragment as used herein comprises a HCVR and a LCVR which confers antigen-binding specificity to VEGFR2 (i.e., a "VEGFR2 binding fragment").

As used herein, the term "light chain variable region (LCVR)" refers to a portion of a light chain of an antibody molecule that includes amino acid sequences of Complementarity Determining Regions (CDRs; ie., CDR1, CDR2, and CDR3), and Framework Regions (FRs).

As used herein, the term "heavy chain variable region (HCVR)" refers to a portion of a heavy chain of an antibody molecule that includes amino acid sequences of Complementarity Determining Regions (CDRs; ie., CDR1, CDR2, and CDR3), and Framework Regions (FRs).

As used herein, the terms "complementarity determining region" and "CDR", refer to the non-contiguous antigen combining sites found within the variable region of LC and HC polypeptides of an antibody or an antigen-binding fragment thereof. These particular regions have been described by others including Kabat, et al., *Ann. NY Acad. Sci.* 190:382-93 (1971); Kabat et al., *J. Biol. Chem.* 252: 6609-6616 (1977); Kabat, et al., *Sequences of Proteins of Immunological Interest*, Fifth Edition, U.S. Department of Health and Human Services, NIH Publication No. 91-3242 (1991); Chothia, et al., J. Mol. Biol. 196:901-917 (1987); MacCallum, et al., J. Mol. Biol., 262:732-745 (1996); and North, et al., J. Mol. Biol., 406, 228-256 (2011), where the definitions include overlapping or subsets of amino acid residues when compared against each other.

The CDRs are interspersed with regions that are more conserved, termed framework regions ("FR"). Each LCVR and HCVR is composed of three CDRs and four FRs, arranged from amino-terminus to carboxy-terminus in the following order: PRE CDR1, FR2, CDR2, FR3, CDR3, FR4. The three CDRs of the light chain are referred to as "LCDR1, LCDR2, and LCDR3" and the three CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions is in accordance with known conventions (e.g., Kabat (1991), Chothia (1987), and/or North (2011)). In different embodiments of the invention, the FRs of the antibody may be identical to the human germline sequences, or may be naturally or artificially modified.

As used herein, the term "DC101" refers to a rat monoclonal antibody directed against mouse VEGFR2 that may be used in experiments as a surrogate in mice for an anti-VEGFR2 Ab, preferably ramucirumab. See, for example, Witte L., et al. Monoclonal antibodies targeting the VEGF receptor-2 (Flk1/KDR) as an anti-angiogenic therapeutic strategy. *Cancer Metastasis Rev.*, 17: 155-161, 1998; and/or Prewett M., et al., Antivascular endothelial growth factor receptor (fetal liver kinase 1) monoclonal antibody inhibits tumor angiogenesis and growth of several mouse and human tumors. Cancer Res., 59: 5209-5218, 1999.

In certain embodiments, the anti-VEGFR2 Ab provided herein for the methods of the present invention is altered to increase or decrease the extent to which the antibody is glycosylated. Addition or deletion of glycosylation sites to an antibody may be conveniently accomplished by altering the amino acid sequence such that one or more glycosylation sites is created or removed.

Where the anti-VEGFR2 Ab comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, anti-VEGFR2 Ab variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; and Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4): 680-688 (2006); and WO2003/085107).

As used herein, the term "kit" refers to a package comprising at least two separate containers, wherein a first container contains [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, and a second container contains an anti-VEGFR2 Ab. As used herein, the term "kit" also refers to a package comprising at least two separate containers, wherein a first container contains [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, and a second container contains ramucirumab. A "kit" may also include instructions to administer all or a portion of the contents of these first and second containers to a cancer patient, preferably a NSCLC patient.

As used herein, the terms "treating," "to treat," or "treatment" refers to restraining, slowing, stopping, reducing, or reversing the progression or severity of an existing symptom, disorder, condition, or disease.

As used herein, the term "patient" refers to a mammal, preferably a human.

As used herein, the terms "cancer" and "cancerous" refer to or describe the physiological condition in patients that is typically characterized by unregulated cell proliferation. Included in this definition are benign and malignant cancers. By "early stage cancer" or "early stage tumor" is meant a cancer that is not advanced or metastatic or is classified as a Stage 0, I, or II cancer. Examples of cancer include, but are not limited to, NSCLC.

A main advantage of the combination treatments of the invention is the ability of producing marked anti-cancer effects in a patient without causing significant toxicities or adverse effects, so that the patient benefits from the combination treatment method overall. The efficacy of the combination treatment of the invention can be measured by various endpoints commonly used in evaluating cancer treatments, including but not limited to, tumor regression, tumor weight or size shrinkage, time to progression, overall survival, progression free survival, overall response rate, duration of response, and quality of life. The therapeutic agents used in the invention may cause inhibition of metastatic spread without shrinkage of the primary tumor, may induce shrinkage of the primary tumor, or may simply exert a tumoristic effect. Because the invention relates to the use of a combination of unique anti-tumor agents, novel approaches to determining efficacy of any particular combination therapy of the present invention can be optionally employed, including, for example, measurement of plasma or urinary markers of angiogenesis and measurement of response through radiological imaging.

As used herein, the term "Complete Response" (CR) refers to the disappearance of all target lesions. Any pathological lymph nodes (whether target or non-target) must have reduction in short axis to <10 mm.

As used herein, the term "Partial Response" (PR) refers to at least a 30% decrease in the sum of diameters of target lesions, taking as reference the baseline sum diameters.

As used herein, the term "Progressive Disease" (PD) refers to at least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm (Note: the appearance of one or more new lesions is also considered progression).

As used herein, the term "Stable Disease" (SD) refers to neither sufficient shrinkage to qualify for PR nor sufficient increase to qualify for PD, taking as reference the smallest sum diameters while on study.

As used herein, the term "Objective Response" (OR) refers to the sum of CR plus PR.

The skilled artisan will appreciate the terms CR, PR, PD, SD and OR correspond to definitions according to RECIST v1.1, Eisenhauer et al., *European Journal of Cancer*, 2009, 45, 228-247.

As used herein, the term "time to disease progression" or "TTP" refers to the time, generally measured in weeks or months, from the time of initial treatment, until the cancer progresses or worsens. Such progression can be evaluated by the skilled clinician.

As used herein, the term "extending TTP" refers to increasing the time to disease progression in a treated patient relative to i) an untreated patient or relative, or ii) a patient treated with less than all of the anti-tumor agents in a particular combination therapy.

As used herein, the term "survival" refers to the patient remaining alive, and includes overall survival as well as progression free survival.

As used herein, the term, "overall survival" refers to the patient remaining alive for a defined period of time, such as 1 year, 5 years, etc from the time of diagnosis or treatment.

As used herein, the term, "progression free survival" refers to the patient remaining alive, without the cancer progressing or getting worse.

As used herein, the term "extending survival" is meant increasing overall or progression free survival in a treated patient relative to i) an untreated patient, ii) a patient treated with less than all of the anti-tumor agents in a particular combination therapy, or iii) a control treatment protocol. Survival is monitored for at least about one month, at least about one month, at least about two months, at least about four months, at least about six months, at least about nine months, or at least about 1 year, or at least about 2 years, or at least about 3 years, or at least about 4 years, or at least about 5 years, or at least about 10 years, etc., following the initiation of treatment or following the initial diagnosis of cancer.

As used herein, the term "primary tumor" or "primary cancer" is meant the original cancer and not a metastatic lesion located in another tissue, organ, or location in the subject's body.

As used herein, the term "effective amount" refers to the amount or dose of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, and to the amount or dose of an anti-VEGFR2 Ab which, upon single or multiple dose administration to the patient, provides an effective response in the patient under diagnosis or treatment. As used herein, the term "effective amount" also refers to the amount or dose of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, and to the amount or dose of ramucirumab, which, upon single or multiple dose administration to the patient, provides an effective response in the patient under diagnosis or treatment. It is understood that a combination therapy of the present invention is carried out by administering [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, together with an anti-VEGFR2 Ab in any manner which provides effective levels of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or a pharmaceutically acceptable salt thereof and the anti-VEGFR2 Ab in the body. It is also understood that a combination therapy of the present invention is carried out by administering [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, together with ramucirumab in any manner which provides effective levels of [5-(4-ethyl-piperazin-1-ylmethyl)-pyridin-2-yl]-[5- fluoro-4-(7-fluoro-3-isopropyl-2-methyl-3H-benzoimidazol-5-yl)-pyrimidin-2-yl]-amine or a pharmaceutically acceptable salt thereof and ramucirumab in the body.

As used herein, the term "effective response" of a patient or a patient's "responsiveness" to treatment with a combination of agents and similar wording refers to the clinical or therapeutic benefit imparted to a patient upon co-administration of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or a pharmaceutically acceptable salt thereof and the anti-VEGFR2 Ab. As used herein, the term "effective response" of a patient or a patient's "responsiveness" to treatment with a combination of agents and similar wording also refers to the clinical or therapeutic benefit imparted to a patient upon co-administration of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or a pharmaceutically acceptable salt thereof and ramucirumab. Such benefit includes any one or more of: extending survival (including overall survival and progression free survival); resulting in an objective response (including a complete response or a partial response); or improving signs or symptoms of cancer, etc.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or a pharmaceutically acceptable salt thereof is generally effective over a wide dosage range in the combination of the present invention. For example, dosages per day normally fall within the range of about 100 mg/day to about 400 mg/day, preferably about 200 mg/day to about 400 mg/day, and most preferably about 300 mg/day to about 400 mg/day. In addition, an anti-VEGFR2 Ab, preferably ramucirumab, is generally effective over a wide dosage range in the combination of the present invention. For example, dosages per three-week cycle normally fall within the range of about 6 to 10 mg/kg, preferably about 8 to about 10 mg/kg, and most preferably about 10 mg/kg. In some instances dosage levels below the lower limit of the aforesaid ranges for [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or a pharmaceutically acceptable salt thereof and an anti-VEGFR2 Ab, preferably ramucirumab, may be more than adequate, while in other cases smaller or still larger doses may be employed with acceptable side effects, and therefore the above dosage range is not intended to limit the scope of the invention in any way. When given in combination with an anti-VEGFR2 Ab, for example, over a 21-day cycle, [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or a pharmaceutically acceptable salt thereof is administered daily within the range of about 100 mg/day to about 400 mg/day and an anti-VEGFR2 Ab, preferably ramucirumab, is administered on day one within the range of about 6 to 10 mg/kg. When given in combination, for example, over a 21-day cycle, [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or a pharmaceutically acceptable salt thereof is administered daily within the range of about 200 mg/day to about 400 mg/day and an anti-VEGFR2 Ab, preferably ramucirumab, is administered on day one within the range of about 8 to 10 mg/kg. When given in combination, for example, over a 21-day cycle, [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or a pharmaceutically salt thereof is administered daily within the range of about 300 mg/day to about 400 mg/day and an anti-VEGFR2 Ab, preferably ramucirumab, is administered on day one at about 10 mg/kg.

The free base, 5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, is preferred. However, it will be understood by the skilled reader that 5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine is capable of forming salts. 5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); L. D. Bighley, S. M. Berge, D. C. Monkhouse, in "Encyclopedia of Pharmaceutical Technology'. Eds. J. Swarbrick and J. C. Boylan, Vol. 13, Marcel Dekker, Inc., New York, Basel, Hong Kong 1995, pp. 453-499; S. M. Berge, et al., "Pharmaceutical Salts", *Journal of Pharmaceutical Sciences*, Vol 66, No. 1, January 1977. The hydrochloride and mesylate salts are preferred salts. The mesylate salt is an especially preferred salt.

[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or a pharmaceutically acceptable salt thereof and an anti-VEGFR2 Ab, preferably ramucirumab, are preferably formulated as pharmaceutical compositions administered by any route which makes the compound bioavailable. The route of administration may be varied in any way, limited by the physical properties of the drugs and the convenience of the patient and the caregiver. Preferably, [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or a pharmaceutically acceptable salt thereof is administered orally. Preferably, an anti-VEGFR2 Ab, preferably ramucirumab, compositions are formulated for parenteral administration, such as intravenous or subcutaneous administration. In addition, [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or pharmaceutically acceptable salt thereof, is formulated for oral or parenteral administration, including intravenous or subcutaneous administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

As used herein, the phrase "in combination with" refers to the administration of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, with an anti-VEGFR2 Ab simultaneously. As used herein, the phrase "in combination with" also refers to the administration of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, with an anti-VEGFR2 Ab sequentially in any order. As used herein, the phrase "in combination with" also refers to the administration of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, with an anti-VEGFR2 Ab in any combination thereof. As used herein, the phrase "in combination with" also refers to the administration of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, with ramucirumab simultaneously. As used herein, the phrase "in combination with" also refers to the administration of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, with ramucirumab sequentially in any order. As used herein, the phrase "in combination with" refers to the administration of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, with ramucirumab in any combination thereof. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine and an anti-VEGFR2 Ab may be administered either as part of the same pharmaceutical composition or in separate pharmaceutical compositions. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine and ramucirumab may be administered either as part of the same pharmaceutical composition or in separate pharmaceutical compositions. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered prior to administration of an anti-VEGFR2 Ab. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered at the same time as administration of an anti-VEGFR2 Ab. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered subsequent to administration of an anti-VEGFR2 Ab. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered prior to, at the same time as, or subsequent to administration of an anti-VEGFR2 Ab or in some combination thereof. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered prior to administration of ramucirumab. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered at the same time as administration of ramucirumab. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered subsequent to administration of ramucirumab. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered prior to, at the same time as, or subsequent to administration of ramucirumab, or in some combination thereof. Where an anti-VEGFR2 Ab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered prior to each administration of an anti-VEGFR2 Ab. Where an anti-VEGFR2 Ab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered at the same time as each administration of an anti-VEGFR2 Ab. Where an anti-VEGFR2 Ab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered subsequent to each administration of an anti-VEGFR2 Ab. Where an anti-VEGFR2 Ab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered prior to, at the same time as, or subsequent to, each administration of an anti-VEGFR2 Ab or some combination thereof. Where an anti-VEGFR2 Ab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered at different intervals in relation to therapy with an anti-VEGFR2 Ab. Where an anti-VEGFR2 Ab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a single or series of dose(s) prior to, at any time during, or subsequent to the course of treatment with an anti-VEGFR2 Ab. Where an anti-VEGFR2 Ab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a single dose prior to, at any time during, or subsequent to the course of treatment with an anti-VEGFR2 Ab Where an anti-VEGFR2 Ab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a single dose prior to the course of treatment with an anti-VEGFR2 Ab. Where an anti-VEGFR2 Ab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a single dose at any time during the course of treatment with an anti-VEGFR2 Ab. Where an anti-VEGFR2 Ab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a single dose subsequent to the course of treatment with an anti-VEGFR2 Ab. Where an anti-VEGFR2 Ab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a series of doses prior to the course of treatment with an anti-VEGFR2 Ab. Where an anti-VEGFR2 Ab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a series of doses subsequent to the course of treatment with an anti-VEGFR2 Ab.

Where ramucirumab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered prior to each administration of ramucirumab. Where ramucirumab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered at the same time as each administration of ramucirumab. Where ramucirumab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered subsequent to each administration of an ramucirumab. Where ramucirumab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered prior to, at the same time as, or subsequent to, each administration of ramucirumab or some combination thereof. Where ramucirumab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered at different intervals in relation to therapy with ramucirumab. Where ramucirumab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a single or series of dose(s) prior to, at any time during, or subsequent to the course of treatment with ramucirumab. Where ramucirumab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a single dose prior to, at any time during, or subsequent to the course of treatment with ramucirumab. Where ramucirumab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a single dose prior to the course of treatment with ramucirumab. Where ramucirumab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a single dose at any time during the course of treatment with ramucirumab. Where ramucirumab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a single dose subsequent to the course of treatment with ramucirumab. Where ramucirumab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a series of doses prior to the course of treatment with ramucirumab. Where ramucirumab is administered at repeated intervals (e.g. during a standard course of treatment), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine can be administered in a series of doses subsequent to the course of treatment with ramucirumab.

[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or pharmaceutically acceptable salts thereof, may be prepared by a variety of procedures known in the art.

The following preparations and examples further illustrate the invention. Unless noted to the contrary, the compounds illustrated herein are named and numbered using ChemDraw® Ultra 5.0.

Preparation 1

1-(6-Bromo-pyridin-3-ylmethyl)-4-ethyl-piperazine

Add neat 1-ethylpiperazine (5.6 kg) to a mixture of 6-bromo-pyridine-3-carbaldehyde (8.3 kg) and dichloromethane (186 kg). Then, add sodium triacetoxyborohydride (10.9 kg) in portions and stir at 20-30° C. for 12 hours. Quench the reaction into a mixture of dichloromethane (36 kg) and aqueous solution of sodium hydroxide 2 N (46 kg). Separate the layers and extract twice the aqueous layer with dichloromethane (24×2 kg). Combine the organic layers, wash with brine (50×2 kg) and remove the solvent under vacuum to afford 11.5 kg of the title compound. MS (ES$^+$): m/z=285 (M+H)$^+$.

Preparation 2

5-(4-Ethyl-piperazin-1-ylmethyl)-pyridin-2-ylamine

Add liquid ammonia (50.0 kg) to a degassed mixture of 1-(6-bromo-pyridin-3-ylmethyl)-4-ethyl-piperazine (14.2 kg), cuprous oxide (200 g), and MeOH (57 kg) at T 40° C. Heat the mixture at 65-75° C. overnight. Cool to 20-30° C. and filter over a CELITE® pad. Concentrate the filtrate and add dichloromethane (113 kg) and adjust the pH to 12-14 with sodium hydroxide 2N (23 kg) separate the phases and wash the organic phase with dichloromethane (58×2 kg) and combine the organic layers. Filter the mixture through CELITE® and concentrate. Dissolve the residue in toluene (9.7 kg) and crystallize by the addition of methyl tert-butyl ether (8.3 kg) to give 6.0 kg of the title compound. Obtain further purification through a toluene recrystallization. MS (ES$^+$): m/z=221 (M+H)$^+$.

Preparation 3

N-(4-Bromo-2,6-difluoro-phenyl)-N'-isopropyl-acetamidine

Add triethylamine (10.05 mL) to a mixture of 4-bromo-2,6-difluoro-phenylamine (10.0 g), N-isopropyl acetamide (9.73 g), phosphoryl chloride (6.70 mL) in toluene (150 mL). Heat the mixture to reflux for 3 hours. Cool the mixture and remove the solvent under vacuum. Dissolve the crude in dichloromethane, wash with an aqueous saturated solution of sodium bicarbonate several times to remove all traces of acid. Dry over sodium sulfate and remove the solvent under vacuum to afford 14 g of the title compound. MS (ES$^+$): m/z=292 (M+H)$^+$.

Preparation 4

6-Bromo-4-fluoro-1-isopropyl-2-methyl-1H-benzo-imidazole

Add potassium tert-butoxide (6.9 kg) in portions to a solution of N-(4-bromo-2,6-difluoro-phenyl)-N'-isopropyl-acetamidine (16.2 kg) in N-methyl formamide (76 kg) while maintaining the temperature at T<30° C. Heat the mixture at 70-75° C. until complete by HPLC. Cool to 20-30° C. and quench by adding into water (227 kg) then extract with methyl tert-butyl ether (37×4 kg). Wash the combined organic phases with brine (49×2 kg) and concentrate to 25-30 L, add n-hexane (64 kg) and filter the slurry to give 11 kg of the title compound. MS (ES$^+$): m/z=272 (M+H)$^+$.

Obtain additional purification by dissolving the crude compound in dichloromethane and filtering through a silica gel and CELITE® pad followed by isolation from a methyl tert-butyl ether/hexane mixture.

Preparation 5

4-Fluoro-1-isopropyl-2-methyl-6-(4,4,5,5-tetram-ethyl-[1,3,2]dioxaborolan-2-yl)-1H-benzoimidazole Bubble nitrogen into a mixture of 6-bromo-4-fluoro-1-isopropyl-2-methyl-1H-benzoimidazole (30.0 g), bis(pina-colato)diboron (42.15 g), tricyclohexylphosphine (5.43 g), potassium acetate (32.58 g), and dimethylsulfoxide (200 mL). Add palladium acetate (2.8 g) and heat in pre-heated oil bath at 90° C. for 1 hour. Dilute with ethyl acetate (200 mL) and filter over a CELITE® pad. Wash the mixture with brine (100 mL), dry over sodium sulfate and remove the solvent under vacuum. Triturate with hexane and filter the solid to afford 27 g of the title compound. MS (ES$^+$): m/z=319 (M+H)$^+$.

Preparation 6

6-(2-Chloro-5-fluoro-pyrimidin-4-yl)-4-fluoro-1-isopropyl-2-methyl-1H-benzoimidazole Bubble nitrogen into a mixture of 2,4-dichloro-5-fluoro-pyrimidine (12.7 g), bis(triphenylphosphine)palladium(II) chloride (4.9 g), sodium carbonate 2 M in water (103.7 mL) and 1,2-dimethoxyethane (120 mL). Heat in a pre-heated oil bath at 80° C. and add drop wise a solution of 4-fluoro-1-isopropyl-2-methyl-6-(4,4,5,5-tetramethyl-[1,3,2]dioxa-borolan-2-yl)-1H-benzoimidazole (22 g) in 1,2-dimethoxy-ethane (200 mL). Stir the mixture at 84° C. for 1 hour. Cool to room temperature, add ethyl acetate (800 mL) and wash twice with brine (100 mL). Dry over magnesium sulfate and remove the solvent under vacuum. Triturate with acetonitrile to afford 14.4 g of the title compound. MS (ES$^+$): m/z=323 (M+H)$^+$.

REFERENCE EXAMPLE 1

[5-(4-Ethyl-piperazin-1-ylmethyl)-pyridin-2-yl]-[5-fluoro-4-(7-fluoro-3-isopropyl-2-methyl-3H-benzo-imidazol-5-yl)-pyrimidin-2-yl]-amine

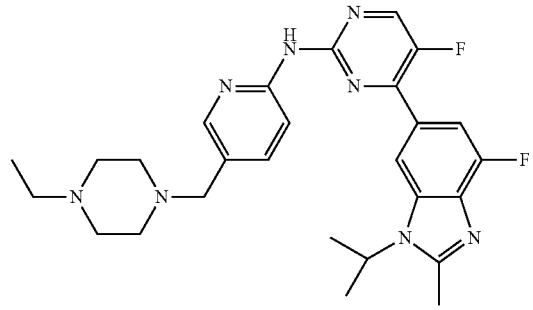 [SMILES: CCN1CCN(Cc2ccc(Nc3ncc(F)c(-c4cc(F)c5nc(C)n(C(C)C)c5c4)n3)nc2)CC1]

Bubble nitrogen into a mixture of 6-(2-chloro-5-fluoro-pyrimidin-4-yl)-4-fluoro-1-isopropyl-2-methyl-1H-benzo-imidazole (15.9 g), 5-(4-ethyl-piperazin-1-ylmethyl)-pyri-din-2-ylamine (10.85 g), cesium carbonate (32.10 g), tris (dibenzylideneacetone) dipalladium (1.82 g), 4,5-bis (diphenylphosphino)-9,9-dimethylxanthene (2.35 g) in 1,4-dioxane (197.06 mL). Heat the mixture in a pre-heated oil bath at 110° C. for 2 hours. Cool to room temperature, dilute with dichloromethane and filter over a CELITE® pad. Remove the solvent under vacuum and purify by silica gel column chromatography, eluting with dichloromethane/methanol (2%) and then dichloromethane/methanol-NH$_3$ 2 M 2% to afford 22.11 g of the title compound. MS (ES$^+$): m/z=507 (M+H)$^+$.

REFERENCE EXAMPLE 1A

[5-(4-Ethyl-piperazin-1-ylmethyl)-pyridin-2-yl]-[5-fluoro-4-(7-fluoro-3-isopropyl-2-methyl-3H-benzo-imidazol-5-yl)-pyrimidin-2-yl]-amine methanesul-fonate Add methanosulfonic acid (63.59 mL) to a solution of [5-(4-ethyl-piperazin-1-ylmethyl)-pyridin-2-yl]-[5-fluoro-4-(7-fluoro-3-isopropyl-2-methyl-3H-benzoimidazol-5-yl) pyrimidin-2-yl]-amine (17.3 g) in a mixture of dichlo-romethane (100 mL) and methanol (100 mL). Stir the solution for 1 hour and remove the solvent under vacuum. Triturate with methyl tert-butyl ether and filtrate the solid to afford 20.4 g of the title compound. MS 35 (ES+): m/z=507 (M+H)$^+$.

REFERENCE EXAMPLE 2

[5-(4-Ethyl-piperazin-1-ylmethyl)-pyridin-2-yl]-[5-fluoro-4-(7-fluoro-3-isopropyl-2-methyl-3H-benzo-imidazol-5-yl)-pyrimidin-2-yl]-amine Crystalline Form I Mix 102.1 mg of amorphous [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine with 2 mL acetone. Isolate the precipitated solid by vacuum filtration, producing a light yellow cake and dry in place on the filtration apparatus for 30 minutes, giving 72.1 mg of a solid. Place the solid in a 100° C. vacuum oven for 3 hours. Representative XRD peaks of Form I are shown in Table 1.

REFERENCE EXAMPLE 3

[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine Crystalline Form III Mix 208 mg of amorphous [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine with 4 mL acetone. Slurry the suspension for 2 hours at 60° C. while stirring at 1000 rpm, and then isolate the solid by vacuum filtration, producing a light yellow cake. Dry in place on the filtration apparatus for 30 minutes, giving 112 mg of a solid (54% yield). Place in an 80° C. vacuum oven for 3 hours. Representative XRD peaks of Form III are shown in Table 2. The peak positions were verified using an external standard.

X-Ray Powder Diffraction

The XRD patterns of the crystals are obtained on a Bruker D8 Advance X-ray powder diffractometer, equipped with a CuKα source (λ=1.54056 Å) and a Vantec detector, operating at 50 kV and 40 mA. Each sample is scanned between 4 and 40° in 2θ, with a step size of 0.02° in 2θ and a scan rate of 9.0 seconds/step, and with 1 mm divergence and receiving slits and a 0.1 mm detector slit. The dry powder is packed into recessed top-loading sample holder and a smooth surface is obtained using a glass slide. The crystal form diffraction patterns are collected at ambient temperature and relative humidity. The background for the Form III crystal is removed prior to peak picking whereas the background is not removed for Form I.

It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.1 in 2θ will take into account these potential variations without hindering the unequivocal identification of the indicated crystal form.

Confirmation of a crystal form may be made based on any unique combination of distinguishing peaks (in units of ° 2θ), typically the more prominent peaks. Thus, a prepared sample of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine Crystalline Form I is characterized by an XRD pattern using CuKα radiation as having diffraction peaks (2-theta values) as described in Table 1 below, and in particular having peaks at 4.51 in combination with one or more of the peaks selected from the group consisting of 13.09, 16.31, and 18.82; with a tolerance for the diffraction angles of 0.1 degrees.

TABLE 1

X-ray powder diffraction peaks of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine Crystalline Form I.

| Angle ° 2θ | d value Angstrom | Intensity % |
|---|---|---|
| 4.51 | 19.60 | 100 |
| 5.89 | 15.00 | 4 |
| 8.98 | 9.84 | 1.5 |
| 11.20 | 7.89 | 2.3 |
| 12.57 | 7.04 | 1.9 |
| 13.09 | 6.76 | 7 |
| 15.93 | 5.56 | 3 |
| 16.31 | 5.43 | 4.4 |
| 17.01 | 5.21 | 1.9 |
| 18.58 | 4.77 | 3.1 |
| 18.82 | 4.71 | 3.6 |
| 20.86 | 4.26 | 1.5 |
| 21.90 | 4.06 | 2.2 |
| 23.12 | 3.84 | 2.4 |
| 23.53 | 3.78 | 3.7 |
| 26.71 | 3.33 | 2.4 |
| 26.85 | 3.32 | 2 |

A prepared sample of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine Crystalline Form III is characterized by an XRD pattern using CuKα radiation as having diffraction peaks (2-theta values) as described in the Table 2 below, and in particular having peaks at 21.29 in combination with one or more of the peaks at 11.54, 10.91, and 12.13; with a tolerance for the diffraction angles of 0.1 degrees.

TABLE 2

X-ray powder diffraction peaks of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine Crystalline Form III.

| Angle ° 2θ | d value Angstrom | Intensity % |
|---|---|---|
| 7.44 | 11.87 | 8 |
| 10.91 | 8.11 | 19 |
| 11.54 | 7.66 | 38 |
| 12.13 | 7.29 | 18 |
| 13.89 | 6.37 | 25 |
| 14.91 | 5.94 | 20 |
| 15.63 | 5.67 | 27 |
| 16.06 | 5.52 | 11 |
| 18.59 | 4.77 | 21 |
| 18.94 | 4.68 | 26 |
| 20.43 | 4.34 | 21 |
| 21.29 | 4.17 | 100 |
| 21.91 | 4.05 | 37 |
| 22.13 | 4.01 | 12 |
| 22.45 | 3.96 | 8 |
| 23.12 | 3.84 | 6 |
| 23.42 | 3.80 | 9 |
| 25.95 | 3.43 | 17 |
| 29.42 | 3.03 | 9 |

Solid-State $^{13}$C NMR

Cross polarization/magic angle spinning (CP/MAS) NMR (solid-state NMR or SSNMR) spectra is obtained on a Bruker Avance III 400 wide-bore NMR spectrometer operating at $^1$H and $^{13}$C frequencies of 400.131 and 100.623

MHz, respectively, and using a Bruker 4 mm double-resonance probe. The MAS rate is set to 5 or 10 kHz using a Bruker MAS-II controller; spinning speeds are maintained within 2 Hz of the set point. SPINAL64 decoupling at a proton nutation frequency of 100 kHz is used for heteronuclear decoupling. Spinning sidebands are eliminated by a five-pulse total sideband suppression (TOSS) sequence. The CP contact time for transferring magnetization from protons to carbons is set to 4 ms and a linear power ramp from 93.5 to 46.9 kHz is used on the $^1$H channel to enhance CP efficiency. The acquisition time is set to 34 ms and spectra are acquired over a spectral width of 30 kHz with a recycle delay of 5 s. The sample temperature is regulated to 297±1 K in order to minimize frictional heating caused by sample spinning. The $^{13}$C chemical shifts are externally referenced (±0.05 ppm) to the proton-decoupled $^{13}$C peak of neat (liquid) tetramethylsilane via the high-field resonance of adamantine (δ=29.5 ppm).

A peak list of chemical shifts for [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine Crystalline Form III is as follows:

$^{13}$C-NMR: ν(F1) (ppm) 11.7, 12.9, 20.5, 48.6, 52.5, 59.4, 108.9, 110.0, 112.7, 127.3, 129.4, 135.5, 136.4, 148.8, 150.1, 152.2, 154.5, 156.3.

REFERENCE EXAMPLE 4

[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine Crystalline Form III—Route B

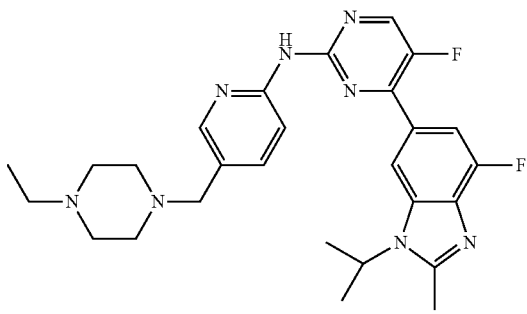 [SMILES: CCN1CCN(Cc2ccc(Nc3ncc(F)c(-c4cc(F)c5nc(C)n(C(C)C)c5c4)n3)nc2)CC1]

a.
1-(6-Bromo-pyridin-3-ylmethyl)-4-ethyl-piperazine

Add neat 1-ethylpiperazine (5.6 kg) to a mixture of 6-bromo-pyridine-3-carbaldehyde (8.3 kg) and dichloromethane (186 kg). Then, add sodium triacetoxyborohydride (10.9 kg) in portions and stir at 20-30° C. for 12 hours. Quench the reaction into a mixture of dichloromethane (36 kg) and aqueous solution of sodium hydroxide 2 N (46 kg). Separate the layers and extract twice the aqueous layer with dichloromethane (24×2 kg). Combine the organic layers, wash with brine (50×2 kg) and remove the solvent under vacuum to afford 11.5 kg of the title compound. MS (ES$^+$): m/z=285 (M+H)$^+$.

b.
5-(4-Ethyl-piperazin-1-ylmethyl)-pyridin-2-ylamine

Add liquid ammonia (50.0 kg) to a degassed mixture of 1-(6-bromo-pyridin-3-ylmethyl)-4-ethyl-piperazine (14.2 kg), cuprous oxide (200 g), and methanol (57 kg) at T≤40° C. Heat the mixture at 65-75° C. overnight. Cool to 20-30° C. and filter over a CELITE® pad. Concentrate the filtrate and add dichloromethane (113 kg) and adjust the pH to 12-14 with sodium hydroxide 2N (23 kg) separate the phases and wash the organic phase with dichloromethane (58×2 kg) and combine the organic layers. Filter the mixture through CELITE® and concentrate. Dissolve the residue in toluene (9.7 kg) and crystallize by the addition of methyl tert-butyl ether (8.3 kg) to give 6.0 kg of the title compound. Obtain further purification through a toluene recrystallization. MS (ES$^+$): m/z=221 (M+H)$^+$.

c. N-Isopropyl-acetamide

Add potassium carbonate (28 kg) to a solution of 2-propanamine (12 kg) in ethyl acetate (108 kg) at <20° C. Cool the mixture to 5-0° C. and add acetyl chloride (16.7 kg) at about 2-3 kg/hour. Stir until complete by gas chromatography. Quench the reaction with water (0.8 kg) and filter the reaction mixture and concentrate to afford 13.4 kg of the title compound. NMR (CDCl$_3$) 4.06 (m, 1H), 1.94 (s, 3H), 1.14 (d, 6H).

d. N-(4-Bromo-2,6-difluoro-phenyl)-N'-isopropyl-acetamidine

Add phosphoryl chloride (16.0 kg) to a mixture of 4-bromo-2,6-difluoro-phenylamine (14.5 kg), N-isopropyl acetamide (8.5 kg), triethylamine (10.6 kg) in toluene (115 kg) at <20° C. Stir at 10-20° C. until complete by high performance liquid chromatography. Remove the solvent under vacuum and add methyl tert-butyl ether (64 kg). Adjust the pH of the mixture with 10% aq. sodium carbonate (250 kg). Filter the mixture and rinse the cake with methyl tert-butyl ether (11×2 kg). Separate the phases and wash the aqueous layer with methyl tert-butyl ether (22×2 kg). Combine the organic layers and concentrate, filter and wash with cyclohexane (0.6 kg) and dry to afford 17.2 kg of the title compound. MS (ES$^+$): m/z=292 (M+H)$^+$.

e. 6-Bromo-4-fluoro-1-isopropyl-2-methyl-1H-benzoimidazole

Add potassium tert-butoxide (6.9 kg) in portions to a solution of N-(4-bromo-2,6-difluoro-phenyl)-N'-isopropyl-acetamidine (16.2 kg) in N-methyl formamide (76 kg) while maintaining the temperature at T<30° C. Heat the mixture at 70-75° C. until complete by high performance liquid chromatography. Cool to 20-30° C. and quench by adding into water (227 kg) then extract with methyl tert-butyl ether (37×4 kg). Wash the combined organic phases with brine (49×2 kg) and concentrate to 25-30 L, add n-hexane (64 kg) and filter the slurry to give 11 kg of the title compound. MS (ES$^+$): m/z=272 (M+H)$^+$.

Obtain additional purification by dissolving the crude compound in dichloromethane and filtering through a silica gel and CELITE® pad followed by isolation from a methyl tert-butyl ether/hexane mixture.

f. 4-Fluoro-1-isopropyl-2-methyl-6-(4,4,5,5-tetramethyl-[1,3,2]dioxaborolan-2-yl)-1H-benzoimidazole Bubble nitrogen into a mixture of 6-bromo-4-fluoro-1-isopropyl-2-methyl-1H-benzoimidazole (600 g), bis(pinacolato)diboron (843 g), tricyclohexylphosphine (106 g), potassium acetate (652 g), and dimethylsulfoxide (3.6 L). Add palladium acetate (49 g) and heat at 100° C. until complete by high performance liquid chromatography. Cool the reaction mixture and dilute with water (18 L), then filter to isolate the solid. Dissolve the crude material in 1,2-dimethoxyethane (450 mL) and filter through CELITE®. Use the filtrate directly in part g.

g. 6-(2-Chloro-5-fluoro-pyrimidin-4-yl)-4-fluoro-1-isopropyl-2-methyl-1H-benzoimidazole Bubble nitrogen into a mixture of 2,4-dichloro-5-fluoropyrimidine (517 g), sodium carbonate (586 g) in water (1.7 L) and 1,2-dimethoxyethane (3.4 L). Add bis(triphenylphosphine)palladium(II) chloride (4.9 g) and heat the reaction at 80±3° C. and add drop wise a solution of 4-fluoro-1-isopropyl-2-methyl-6-(4,4,5,5-tetramethyl-[1,3,2]dioxaborolan-2-yl)-1H-benzoimidazole in 1,2-dimethoxyethane from part f (5.1 L). Stir the mixture at 80±3° C. until complete by high performance liquid chromatography. Cool to room temperature and dilute with cold water (2.1 L, 5° C.). Stir for 1 hour then isolate the crude solid by filtration. Achieve further purification of the solid by trituration with isopropyl alcohol to give 472 g of the title compound. MS (ES$^+$): m/z=323 (M+H)$^+$.

h. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine Crystalline Form III

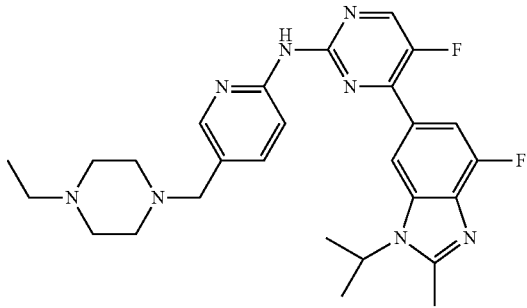 [SMILES: CCN1CCN(Cc2ccc(Nc3ncc(F)c(-c4cc(F)c5nc(C)n(C(C)C)c5c4)n3)nc2)CC1]

Bubble nitrogen into a mixture of 6-(2-chloro-5-fluoro-pyrimidin-4-yl)-4-fluoro-1-isopropyl-2-methyl-1H-benzoimidazole (465 g), 5-(4-ethyl-piperazin-1-ylmethyl)-pyridin-2-ylamine (321 g), potassium carbonate (403 g), 4,5-bis(diphenylphosphino)-9,9-dimethylxanthene (17 g) in t-amyl alcohol (2.3 L). Heat tris(dibenzylideneacetone) dipalladium (13.2 g) and the mixture at 100±5° C. until complete by high performance liquid chromatography. Cool to room temperature, dilute with dichloromethane (1.2 L) and filter over a CELITE® pad. Extract the filtrate with 4M HCl (2.3 L×2). Combine the aqueous layers and stir with charcoal (32 g). Filter through CELITE®, add dichloromethane (1.7 L) and adjust pH with NaOH (28% aq., 1.5 L). Collect the organic layer and wash the aqueous layer with dichloromethane (1.7 L). Combine organic layers, wash with brine (1 L), and dry over magnesium sulphate. Use a solid supported Si-Thiol treatment to remove residual palladium and the solvent is exchanged to acetone. Filter the slurry and dry to give 605 g of crude product as Form I. Mix 605 g of Form I and 4.3 L of dry acetone. Slurry the suspension at 56-57° C. (reflux) for at least 18 hours and then at ambient temperature for 4 hours. Isolate the solid by vacuum filtration, producing a light yellow cake. Dry the solid in a vacuum oven at 35° C. until a constant weight of 570 g is obtained. Confirm the material by XRPD to be Form III of the title compound. MS (ES+): m/z=507 (M+H)+.

The following examples illustrate the unexpected improvement of the combination of an anti-VEGFR2 Ab, including, but not limited to, ramucirumab, (via the rat monoclonal antibody directed against mouse VEGFR2 that may be used in experiments as a surrogate in mice for ramucirumab, DC101) and [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine. The mesylate salt form of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine is used in certain of the following assays and is designated as Compound A.

EXAMPLE 1

Antitumor Effects of Compound A in Combination with DC101 in Mouse Xenograft Models (NCI-H441 and NCI-H2122) for Non-Small Cell Lung Cancer General Information:
Tumor Implantation and Treatment:
Grow the human NSCLC line NCI-H441 or NCI-H2122 in RPMI 1640 medium+10% fetal bovine serum. Harvest sub-confluent cells with trypsin and rinse twice with growth medium without serum. For subcutaneous tumors, initiate growth by subcutaneous injection of $5 \times 10^6$ cells in a 1:1 mixture of Hank's balanced salt solution (HBSS) and Matrigel (BD Bioscience, Franklin Lakes, N.J.) in the rear flank of each subject animal. When mean tumors volumes reach approximately 150-200 mm$^3$ in size, randomize the animals by tumor size and body weight by randomization techniques well known in the art and place into their respective treatment groups using the number of animals per group as indicated.
Data Capture:
Capture tumor size and body weight using Web Director. Estimate tumor volume (V) by using the formula: $V=0.536L \times W^2$ where L=larger of measured diameter and W=smaller of perpendicular diameter. Transform the tumor volume data to a log scale to equalize variance across time and treatment groups. Analyze the log volume data with a two-way repeated measures analysis of variance by time and treatment using the MIXED procedures in SAS software (Version 9.3). The correlation model for the repeated measures is Spatial Power. Compare treated groups compared to the control group at each time point. Use the MIXED procedure also separately for each treatment group to calculate adjusted means and standard errors at each time point. Both analyses account for the autocorrelation within each animal and the loss of data that occurred when animals with large tumors were removed from the study early. Plot the adjusted means and standard errors for each treatment group versus time. Calculate relative changes in tumor volume (% T/C) using the tumor volume measurements taken nearest to the last day of dosing with Compound A, whereas the baseline tumor volume is the volume recorded on or just prior to first day of dosing. Calculate % T/C values using the formula % T/C=100×ΔT/ΔC, whereby T=mean tumor volume of the compound treated group, ΔT=mean tumor volume of the compound treated group minus the mean tumor volume on the baseline day, C=mean tumor volume of the control (vehicle) group, and ΔC=mean tumor volume of the control group minus the mean tumor volume on the baseline day. Tumor growth inhibition is observed in those instances where the calculated values for % T/C are less than 100% whereby greater inhibition results in smaller % T/C values. If ΔT was <0, then a tumor regression value was calculated instead of % T/C whereby % Regression=100×ΔT/T$_{initial}$ such that T$_{initial}$=the grand mean of the tumor volume for all the treatment groups. Any negative values for % T/C listed are values for % Regression.

Assess antitumor efficacy of the combination of DC101 and Compound A by measuring tumor volume by three dimensional caliper measurements twice a week during the course of the study. Measure body weight twice weekly during the course of the study, as a general indicator of tolerability.

Formulations for Compound A and DC101: Formulate Compound A on a weekly basis in 1% hydroxyethyl cellulose (HEC) in 25 mM phosphate buffer (PB) at a pH of 2 and store at 4° C. Solubilize DC101 in phosphate buffered saline and store at 4° C.

Control Group: administer to the animals in the control group, both vehicles used for Compound A and DC101 according to the same schedules for each compound, respectively.

For the monotherapy groups, treat the animals with the desired compound as directed and with the vehicle for the compound not being dosed by following the schedule for the non-dosed compound.

NCI-H441 Xenograft Tumors

Study 1:
Monotherapy Compound A

Treat female Hsd athymic nude mice (n=8) bearing NCI-H441 xenograft tumors with Compound A by oral gavage once daily for 28 days at a dose of 50 or 100 mg/kg using 0.2 mL/dose. Administer Compound A starting after the mean tumor volumes reach approximately 150-200 mm$^3$ in size (day 15 after tumor implantation) and end treatment 28 days later (on day 42). Measure tumor volume and body weight twice a week for the duration of the treatment period.

Results: Treatment with either 50 or 100 mg/kg of Compound A resulted in a significant inhibition of tumor growth. The mean percent regression observed on study day 42 was −8.1% for the 50 mg/kg dose and −22.8% for the 100 mg/kg dose. These values were determined to be statistically significant (p<0.001) as compared to control. Relative tumor volume at the end of the treatment period indicated that treatment with 50 mg/kg of Compound A monotherapy resulted in a partial response in 6/8 animals and stable disease in 2/8 animals. A partial response was observed in all (8/8) mice treated with 100 mg/kg of Compound A monotherapy. No significant tolerability issues were shown with single-agent of Compound A treatment: the maximum relative body weight loss was 4.7% for the 100 mg/kg dose and 2.7% for the 50 mg/kg dose. Body weight loss was measured as the percentage change from the mean body weights recorded on baseline (day 14) versus last day of treatment (day 42).

Monotherapy DC101

Treat female Hsd athymic nude mice (n=8) bearing NCI-H441 xenograft tumors with DC101 twice weekly for four weeks by intraperitoneal injection at doses of 10, 20 or 40 mg/kg. Administer DC101 starting after the mean tumor volumes reach approximately 150-200 mm$^3$ in size (day 15 after tumor implantation) and end on day 39. Measure tumor volume and body weight twice a week for the duration of the treatment period.

Results: Treatment with 10, 20, or 40 mg/kg of DC101 resulted in a significant inhibition of tumor growth. The changes in tumor volume (% T/C) observed at the end of the dosing period (day 42) were 25.6%, 10.4%, and 9.0% for 10, 20, and 40 mg/kg doses, respectively. Statistically significant (p<0.001) growth inhibition of the NCI-H441 xenograft tumors as compared to the vehicle control group (p<0.001%) was observed for all the groups treated with DC101. Single-agent treatment with DC101 resulted in a dose-dependent trend with regard to the frequency of stable disease and partial responses such that the combined frequency for stable disease and partial response was 2/8, 5/8, and 6/8 in the groups treated with 10, 20, and 40 mg/kg, respectively. There were no significant tolerability issues with any of the single-agent treatments with DC101: the maximum relative body weight loss was 1.3% for the 10 mg/kg dose, 1.5% for the 20 mg/kg dose, and 0.5% for the 40 mg/kg dose. Body weight loss was measured as the percentage change from the mean body weights recorded on baseline (day 14) versus last day of treatment (day 42).

Combination with Compound A and DC101

Treat female Hsd athymic nude mice (n=8) bearing NCI-H441 xenograft tumors with Compound A by oral gavage once daily for 28 days at a dose of 50 mg/kg using 0.2 mL/dose and intraperitoneal inject DC101 twice weekly at a dose of 20 mg/kg. Administer both starting on day 15 after tumor implantation, ending Compound A treatment on day 42 and DC101 treatment on day 39. Measure tumor volume twice a week for the duration of the treatment period and measure body weight.

Results: Combined treatment with 50 mg/kg of Compound A and 20 mg/kg of DC101 resulted in an improvement in antitumor efficacy as compared to each of the monotherapy groups. Tumor volume at the end of the dosing period (day 42) showed a 42.9% regression (i.e. % T/C=−42.9%) in the combination group as compared to a 8.1% regression in the group treated with 50 mg/kg of Compound A alone and a an observed % T/C of 10.4% in the group treated with 20 mg/kg of DC101 alone. The difference in the antitumor efficacy between each monotherapy group compared to the combination group was statistically significant (p<0.001). Combination treatment resulted in a partial response in 8/8 of the treated animals. In contrast, only 2/8 animals showed a partial response to DC101 monotherapy, three animals showed stable disease (3/8) and three animals showed progressive disease (3/8). 6/8 animals showed a partial response to Compound A monotherapy and 2 animals showed stable disease (2/8). For combination therapy, there was an increase in the frequency of partial responders (8/8), as well as an statistically significant increase (p<0.001) in the magnitude of regression (5/8 animals receiving combination therapy had regression rates better than the best response observed in the single-agent of Compound A (50 mg/kg) group). No statistically significant changes in tolerability relative to monotherapy or controls were observed with combination treatment. Specifically, the maximum relative body weight loss in the combination group was 3.0% as compared to 2.7% for monotherapy of Compound A treatment and 1.5% for monotherapy DC101 treatment. Body weight loss was measured as the percentage change from the mean body weights recorded on baseline (day 14) versus last day of treatment (day 42).

Study 2:
Monotherapy Compound A

Treat female Hsd athymic nude mice (n=7) bearing NCI-H441 xenograft tumors with Compound A by oral gavage (PO) once daily for 28 days at a dose of 50 or 75 mg/kg using 0.2 mL/dose. Administer Compound A starting after the mean tumor volumes reach approximately 150-200 mm$^3$ in size (day 36 after tumor implantation) and end treatment 28 days later (on day 63). Measure tumor volume and body weight twice a week for the duration of the treatment period.

Results: At the end of the dosing period (Day 67) NCI-H441 xenografts treated with either the 50 or 75 mg/kg of Compound A resulted in significant inhibition of tumor growth. The 50 mg/kg treatment showed % T/C of 7.0% whereas the 75 mg/kg treatment resulted in a regression of −4.8%, when compared to the vehicle controls. These values were determined to be statistically significant (p<0.001) as compared to control. Relative tumor volume at the end of the treatment period indicated that monotherapy with 50 or 75 mg/kg Compound A resulted in a dose-dependent trend with regard to the frequency of stable disease and partial responses such that the combined frequency for stable disease and partial response was 4/7 and 6/7 respectively. 2/7 and 3/7 mice achieved complete regression for the 50 mg/kg and 75 mg/kg Compound A monotherapies. The maximum relative body weight loss was 5.5% and 5.1% for the 50 and 75 mg/kg Compound A monotherapies which was not statistically different from control animals.

Monotherapy DC101

Treat female Hsd athymic nude mice (n=7) bearing NCI-H441 xenograft tumors with DC101 twice weekly for four weeks by intraperitoneal injection at a dose 20 mg/kg. Administer DC101 starting after the mean tumor volumes reach approximately 150-200 mm$^3$ in size (day 36 after tumor implantation). Measure tumor volume and body weight twice a week for the duration of the treatment period.

Results: Treatment with the 20 mg/kg DC101 also resulted in significant inhibition of tumor growth with % T/C of 5.6% when compared to the vehicle controls. These values were determined to be statistically significant (p<0.001) as compared to control. Relative tumor volume at the end of the treatment period indicated that monotherapy with DC101 resulted in 2/6 of mice with progressive disease, 2/6 with stable disease and 2/6 mice achieving a partial response. The maximum relative body weight loss was 3.9% for the DC101 monotherapy which was not statistically different from control animals.

Combination of Compound A and DC101

Treat female Hsd athymic nude mice (n=7) bearing NCI-H441 xenograft tumors with Compound A by oral gavage once daily for 28 days at a dose of 50 mg/kg or 75 mg/kg using 0.2 mL/dose and intraperitoneal inject DC101 twice weekly at a dose of 20 mg/kg. Administer both starting after the mean tumor volumes reach approximately 150-200 mm$^3$ in size (day 36 after tumor implantation) and ending treatment on day 63. Measure tumor volume and body weight twice a week for the duration of the treatment period.

Combination treatment with 20 mg/kg DC101 and Compound A showed antitumor efficacy that was significantly better than any of the monotherapy groups wherein the combination treatments which included either 50 or 75 mg/kg of Compound A resulted in tumor regressions of −48.6% and −38.9%, respectively. These effects on tumor growth were statistically significant when compared to the vehicle control group (p<0.001) as well as to their respective monotherapy groups. In particular, when compared to the DC101 monotherapy, the combination with the 50 or 75 mg/kg were both statistically significant with p<0.001 and p=0.033, respectively; when compared to their respective Compound A monotherapy groups the combination treatments with 50 and 75 mg/kg were also statistically significant with p<0.001 and p=0.006, respectively.

Relative tumor volume measurements at the end of the treatment period indicated that combination therapy of DC101 with 50 or 75 mg/kg Compound A resulted in a disease control rate of 100% whereby 7/7 mice in each group had either stable disease or achieved a partial response. This shows a significant improvement in response as compared to monotherapy with either DC101 or Compound A wherein the disease control rates (stable disease+partial response) observed were 4/7, 6/7, and 4/6 for monotherapy with 50 mg/kg of Compound A, 75 mg/kg of Compound A, and 20 mg/kg of DC101, respectively.

Changes in relative body weight in the combination groups were not statistically different from the control or monotherapy groups.

NCI-H2122 Xenograft Tumors

Monotherapy Compound A

Treat female Hsd athymic nude mice (n=8) bearing NCI-H2122 xenograft tumors with Compound A by oral gavage (PO) once daily for 28 days at a dose of 50 or 75 mg/kg using 0.2 mL/dose. Administer Compound A starting after the mean tumor volumes reach approximately 150-200 mm$^3$ in size (day 16 after tumor implantation) and end treatment on day 43. Measure tumor volume and body weight twice a week for the duration of the treatment period.

Results: At the end of the dosing period (Day 45) NCI-H2122 xenografts treated with either 50 or 75 mg/kg of Compound A resulted in significant inhibition of tumor growth with % T/C of 64.3% and 37.3% respectively, when compared to the vehicle controls. These values were determined to be statistically significant (p<0.001) as compared to control. Changes in relative body weight in the groups which received Compound A were not statistically different from the control group.

Monotherapy DC101

Treat female Hsd athymic nude mice (n=8) bearing NCI-H2122 xenograft tumors with DC101 by intraperitoneal injection at a dose 20 mg/kg. Administer DC101 starting after the mean tumor volumes reach approximately 150-200 mm$^3$ in size (day 16 after tumor implantation) and continue twice weekly for four weeks. Measure tumor volume and body weight twice a week for the duration of the treatment period.

Results: Treatment with the 20 mg/kg DC101 also resulted in significant inhibition of tumor growth with % T/C of 45.7% when compared to the vehicle controls. This value was determined to be statistically significant (p<0.001) as compared to control. Change in relative body weight in the group which received DC101 was not statistically different from the control group.

Combination with Compound A and DC101

Treat female Hsd athymic nude mice (n=8) bearing NCI-H2122 xenograft tumors with Compound A by oral gavage (PO) once daily for 28 days at a dose of 50 or 75 mg/kg using 0.2 mL/dose and intraperitoneal inject DC101 twice weekly at a dose of 20 mg/kg. Administer both starting after the mean tumor volumes reach approximately 150-200 mm$^3$ in size (day 16 after tumor implantation) and ending treatment on day 43. Measure tumor volume and body weight twice a week for the duration of the treatment period.

Results: Combination treatment with 20 mg/kg DC101 and Compound A showed antitumor efficacy that was significantly better than any of the monotherapy groups wherein the combination treatments which included either 50 or 75 mg/kg of Compound A resulted in % T/C of 20.7% and 9.3% respectively. These effects on tumor growth were statistically significant when compared to the vehicle control group (p<0.001) as well as when compared to their respective Compound A monotherapy groups (p<0.001). When compared to the DC101 monotherapy, the combination with the 50 or 75 mg/kg were both statistically significant with p=0.002 and p<0.001 respectively. Relative tumor volume at the end of the treatment period indicated that combination therapy with DC101 and 50 or 75 mg/kg Compound A resulted in a dose-dependent trend with regard to the frequency of stable disease and partial responses such that the combined frequency for stable disease and partial response was 4/8 and 7/8 respectively. Changes in relative body weight in the combination groups were not statistically different from the control or monotherapy groups.

Overall in the 3 different studies, significant antitumor efficacy following monotherapy with both DC101 and Compound A was observed with statistically significant improvements in efficacy resulting with the combination therapy. Body weight measurements taken throughout the course of the 3 studies indicated that none of the treatments, including the combination treatments, had a significant negative impact on tolerability.

EXAMPLE 2

Combinations of Ramucirumab and Anti-CDK4/6 Treatment Reduces Endothelial Cell Sprouting Measure the in vitro reduction of endothelial cell sprouting by an in vitro cell-based assay. Use the assay to measure the effect of Compound A and ramucirumab on endothelial cell sprouting.

Culture HUVEC cells (Lonza #C2519A) in Lonza EBM2 (Lonza #CC-3156) media supplemented with SINGLEQUOTS™ (Lonza #CC-4176) and 2% fetal bovine serum (FBS). Culture lung cancer associated Fibroblast cells (CAF) in Lonza fibroblast basal medium (FBM) (Lonza #CC-3131) media supplemented with SINGLEQUOTS™ (Lonza #CC-4126) and 10% FBS (Hyclone #SH30611.02).

Hydrate 1 gram of Dextran-coated Cytodex 3 microbeads (Sigma #C3275) in 50 mL PBS (HyClone #SH30264.02) for at least 3 hours at room temperature and place on a rocker for 15 minutes. Discard supernatant, wash beads 3× with PBS and re-suspend in 50 mL PBS. Place in a siliconized glass bottle and autoclave for 15 minutes at 120° C. and store at 4° C.

On the day of assay, gently mix beads and transfer 1.2 mL beads to a 50 mL tube (Falcon, #352098), and allow them to settle naturally. Aspirate PBS, and wash beads with 20 mL of pre-warmed complete endothelial basal medium-2 (EBM2). Allow beads to settle, gently aspirate media and add 15 mL of complete EBM2.

Harvest HUVEC cells from culture flasks, rinse with PBS, and add and aspirate TrypLE (Gibco #126051-010) as soon as cells round up. Gently re-suspend HUVEC cells in 20 mL of complete media, determine viable cell count and add $2.5 \times 10^7$ cell suspension to the beads, to a final volume of 24 mL. Place the tube lying down at 37° C. in 5% $CO_2$ for 4 hours, and gently invert several times every 20 minutes. Transfer beads and cell suspension at 2 mL/flask into 12 T75 flasks (Nunc #156499). Rinse the tube with 20 mL of media and split equally amongst the 12 flasks. Bring up media to 10 mL and incubate flasks at 37° C. in 5% $CO_2$ overnight.

Pipette medium containing the HUVEC/beads from 2 T75 flasks up and down several times to free HUVEC/beads from the flask. Transfer the solution to a 50 mL tube and wash the flasks with 5 mL media and transfer to the same tube. Allow beads to settle and further mix 2× with fresh EBM2 using a 1 mL pipette to separate the beads as needed. Re-suspend beads in 2×15 mL of fibrinogen solution, which consists of 50 mL of 2 mg/mL fibrinogen (Sigma #F4883), supplemented with 1875 μL of 4 U/mL Aprotinin (0.15 units/mL final concentration) (Sigma #A3428). Sterile filter with a 0.22 micron filter.

Harvest CAF cells from T150 flasks, rinse with PBS, and add and aspirate TrypLE (Gibco #126051-010) as soon as cells round up. Add 2 mL of complete medium (EBM2 supplemented with SINGLEQUOTS™ and 2% FBS) and determine viable cell count and add cells at $4 \times 10^4$ cells/mL to the fibrinogen solution.

Add 12 μL of thrombin (Sigma #T4393-100 units) to a final concentration of 0.6 units/0.5 mL of clot solution to 24-well glass bottom plates (In Vitro Scientific #P24-1.5H-N). Quickly add 0.5 mL of fibrinogen-bead/CAF suspension to each well to allow mixing and prevent bubble formation. Place plates in the hood for 20 minutes to clot without disturbance, and then move the plates to an incubator (37° C., 5% $CO_2$) for 20 minutes. Add 0.5 mL of complete media drop wise to each well to avoid disrupting the clot. Add ramucirumab at a concentration of 10 μg/mL to each well. Add Compound A to ramucirumab containing wells at concentrations of 3, 10, 30, 100 and 500 nM. Serially dilute compounds in dimethyl sulfoxide and then transfer to the assay plate such that the final concentration of the dimethyl sulfoxide in the assay is 0.05%. Incubate plates at 37° C. in 2% $CO_2$. At day 4 post-treatment, replace medium with fresh media and treatments.

At day 7 post-treatment, fix wells overnight at 4° C. in 4% paraformaldehyde (PFA) (Electron Microscopy Sciences #15710). Wash plates with 0.5 mL of Dulbecco's Phosphate-Buffered Saline (DPBS) (HyClone SH30264.01, Lot # AVJ79791) and permeabilize with 0.5% TRITON™ X-100/PBS (Sigma #T9284) for 10 minutes at 4° C. Rinse plates 3× for 10-15 minutes each with 1 mL of glycine/DPBS (Bio-Rad #161-0718) and block overnight with 0.5 mL per well of IF Buffer consisting of 0.1% BSA, 0.2% TRITON™ X-100, 0.05% Tween-20 in DPBS+10% goat serum (Invitrogen #16210). Remove buffer and incubate plates overnight at 4° C. with primary antibodies, sheep anti-human CD31 (1:100) (R&D Systems #BAF806) and anti-α smooth muscle actin, Cy3 labeled (1:200) (Sigma #C6198) in above buffer. Rinse wells 3× for 20 minutes each with IF Buffer at room temperature with gentle rocking. Add Alexa Fluor 488 Donkey anti-sheep IgG (H+L) (1:200) (Molecular Probes #A-11015) in incubation buffer and incubate at room temperature for 1 hour. Rinse wells as above, and incubate in 4',6-diamidino-2-phenylindole (DAPI)(1:10000) (Invitrogen #D1306) in DPBS for 1 to 2 hours at room temperature. Rinse wells with DPBS for 5 minutes. Add 0.5 mL of DPBS and scan plates on CELLINSIGHT™ (Thermal Science) using 2× Objective. Use the CELLINSIGHT™ neurite detection assay for imaging and quantitation of endothelial cell sprouting. Statistically analyze data using JMP 9 (SAS, 9.0.3).

Each experiment represents the mean of triplicates which is expressed as the geometric means and 95% confidence intervals may be calculated. Percent Reduction is calculated with the formula ((ramucirumab control-treated)/(ramucirumab control))*100.

The results suggest that the addition of Compound A to ramucirumab, dose dependently added to the anti-vascular effects of ramucirumab. Compound A in combination with ramucirumab reduced endothelial sprouting length by 42.5% (p<0.0034) and 50% (p<0.0007) at 300 nM and 500 nM respectively when compared to ramucirumab treatment alone.

EXAMPLE 3

A Study of [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine in Combination with Ramucirumab for Patients with Stage IV NSCLC Study Design This study is a multicenter, nonrandomized, open-label, dose-escalation Phase 1b study of oral dosing of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine at 100 mg, 150 mg, or 200 mg every 12 (±3) hours on Days 1 through 21 of a 21-day cycle. in combination with ramucirumab administered at 10 mg/kg over a 60-minute IV infusion followed by a 1-hour observation period on Day 1 of a 21-day cycle for patients with Stage IV NSCLC.

Study Objectives

The primary objective of this study is to evaluate the safety and tolerability of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine when administered orally in combination with ramucirumab to patients with Stage IV NSCLC using Common Terminology Criteria for Adverse Events (CTCAE version 4.0, NCI 2009).

The secondary objectives of the study are to document the antitumor activity of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine when given in combination with ramucirumab; to determine the pharmacokinetics (PK) of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine when given in combination with ramucirumab; and to characterize changes in patient-reported pain and disease-related symptoms collected via the MD Anderson Symptom Inventory-Lung Cancer (MDASI-LC).

Trial Drugs

[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine is supplied as capsules at 100 mg, 150 mg, or 200 mg for oral administration.

Contingency for de-escalation of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine to 100 mg orally every 12 hours on Days 1 through 21 of a 21-day cycle will be permitted.

Ramucirumab is supplied in a sterile, preservative-free solution for infusion of ramucirumab formulated in an aqueous solution at a concentration of 10 mg/kg (500 mg/50-mL vial). The buffer contains 10 mM histidine, 75 mM sodium chloride, 133 mM glycine, and 0.01% polysorbate 80, pH 6.0. Ramucirumab is supplied in single-use 50-mL nominal volume glass vials.

The first dose of ramucirumab is dependent upon the patient's baseline body weight in kilograms. Subsequent doses of ramucirumab must be recalculated if there is a ≥10% change (increase or decrease) in body weight from last dose calculation; subsequent doses may be recalculated if there is a <10% change (increase or decrease) in body weight from last dose calculation.

Preliminary data on evaluable patients from an ongoing clinical trial are presented in Table 3.

TABLE 3

| abemaciclib (mg) | Patient | Study Day of Response Assessment | Target Response | Overall Response | EGFR Status | KRAS Mutation Status |
| --- | --- | --- | --- | --- | --- | --- |
| 150 | 1 | 172 | PR | PR | Negative | Positive |
|  | 2 | 36 | NDR | PD | NDR | NDR |
|  | 3 | 37 | SD | SD | Negative | NDR |
| 200 | 4 | 42 | SD | SD | Negative | Positive |
|  | 5 | 41 | SD | SD | Positive | NDR |
|  | 6 | 86 | PD | PD | Negative | Negative |
|  | 7 | 44 | PR | PR | NDR | NDR |
|  | 8 | 84 | NDR | SD | NDR | NDR |

PR is partial response;
SD is stable disease;
PD is progressive disease;
NDR is no data reported.

Although the above preliminary data on evaluable patients reveals two patients with progressive disease, it further reveals four patients with stable disease and two patients with partial response.

SEQUENCE LISTING

<SEQ ID NO: 1; DNA; human>
GACATCCAGATGACCCAGTCTCCATCTTCCGTGTCTGCATCTATAGGAGA
CAGAGTCACCATCACTTGTCGGGCGAGTCAGGGTATTGACAACTGGTTAG
GCTGGTATCAGCAGAAACCTGGGAAAGCCCCTAAACTCCTGATCTACGAT
GCATCCAATTTGGACACAGGGGTCCCATCAAGGTTCAGTGGAAGTGGATC
TGGGACATATTTTACTCTCACCATCAGTAGCCTGCAAGCTGAAGATTTTG
CAGTTTATTTCTGTCAACAGGCTAAAGCTTTTCCTCCCACTTTCGGCGGA
GGGACCAAGGTGGACATCAAA <SEQ ID NO: 2; PRT1; human>
DIQMTQSPSSVSASIGDRVTITCRASQGIDNWLGWYQQKPGKAPKLLIYD
ASNLDTGVPSRFSGSGSGTYFTLTISSLQAEDFAVYFCQQAKAFPPTFGG
GTKVDIK

SEQUENCE LISTING

<SEQ ID NO: 3; DNA; human>
GAGGTCCAGCTGGTGCAGTCTGGGGGAGGCCTGGTCAAGCCTGGGGGGTC
CCTGAGACTCTCCTGTGCAGCCTCTGGATTCACCTTCAGTAGCTATAGCA
TGAACTGGGTCCGCCAGGCTCCAGGGAAGGGGCTGGAGTGGGTCTCATCC
ATTAGTAGTAGTAGTAGTTACATATACTACGCAGACTCAGTGAAGGGCCG
ATTCACCATCTCCAGAGACAACGCCAAGAACTCACTGTATCTGCAAATGA
ACAGCCTGAGAGCCGAGGACACGGCTGTGTATTACTGTGCGAGAGTCACA
GATGCTTTTGATATCTGGGGCCAAGGGACAATGGTCACCGTCTCAAGC <SEQ ID NO: 4; PRT1; human>
EVQLVQSGGGLVKPGGSLRLSCAASGFTFSSYSMNWVRQAPGKGLEWVSS
ISSSSSYIYYADSVKGRFTISRDNAKNSLYLQMNSLRAEDTAVYYCARVT
DAFDIWGQGTMVTVSS <SEQ ID NO: 5; DNA; human>
GACATCCAGATGACCCAGTCTCCATCTTCCGTGTCTGCATCTATAGGAGA
CAGAGTCACCATCACTTGTCGGGCGAGTCAGGGTATTGACAACTGGTTAG
GCTGGTATCAGCAGAAACCTGGGAAAGCCCCTAAACTCCTGATCTACGAT
GCATCCAATTTGGACACAGGGGTCCCATCAAGGTTCAGTGGAAGTGGATC
TGGGACATATTTTACTCTCACCATCAGTAGCCTGCAAGCTGAAGATTTTG
CAGTTTATTTCTGTCAACAGGCTAAAGCTTTTCCTCCCACTTTCGGCGGA
GGGACCAAGGTGGACATCAAACGAACTGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCAAGGACAGCACCTACAGCCTCAGCAGCACCCTGACGCTGAGCAAAG
CAGACTACGAGAAACACAAAGTCTACGCCTGCGAAGTCACCCATCAGGGC
CTGAGCTCGCCCGTCACAAAGAGCTTCAACAGGGGAGAGTGT <SEQ ID NO: 6; PRT1; human>
DIQMTQSPSSVSASIGDRVTITCRASQGIDNWLGWYQQKPGKAPKLLIYD
ASNLDTGVPSRFSGSGSGTYFTLTISSLQAEDFAVYFCQQAKAFPPTFGG
GTKVDIKRTVAAPSVFIFTPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC <SEQ ID NO: 7; DNA; human>
GAGGTCCAGCTGGTGCAGTCTGGGGGAGGCCTGGTCAAGCCTGGGGGGTC
CCTGAGACTCTCCTGTGCAGCCTCTGGATTCACCTTCAGTAGCTATAGCA
TGAACTGGGTCCGCCAGGCTCCAGGGAAGGGGCTGGAGTGGGTCTCATCC
ATTAGTAGTAGTAGTAGTTACATATACTACGCAGACTCAGTGAAGGGCCG
ATTCACCATCTCCAGAGACAACGCCAAGAACTCACTGTATCTGCAAATGA
ACAGCCTGAGAGCCGAGGACACGGCTGTGTATTACTGTGCGAGAGTCACA
GATGCTTTTGATATCTGGGGCCAAGGGACAATGGTCACCGTCTCAAGCGC
TAGCACCAAGGGCCCATCGGTCCTCCCCCTGGCACCCTCCTCCAAGAGCA
CCTCTGGGGGCACAGCGGCCCTGGGCTGCCTGGTCAAGGACTACTTCCCC
GAACCGGTGACGGTGTCGTGGAACTCAGGCGCCCTGACCAGCGGCGTGCA
CACCTTCCCGGCTGTCCTACAGTCCTCAGGACTCTACTCCCTCAGCAGCG
TGGTGACCGTGCCCTCCAGCAGCTTGGGCACCCAGACCTACATCTGCAAC
GTGAATCACAAGCCCAGCAACACCAAGGTGGACAAGAGAGTTGAGCCCAA
ATCTTGTGACAAAACTCACACATGCCCACCGTGCCCAGCACCTGAACTCC
TGGGGGGACCGTCAGTCTTCCTCTTCCCCCCAAAACCCAAGGACACCCTC
ATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGC
ATAATGCCAAGACAAAGCCGCGGGAGGAGCAGTACAACAGCACGTACCGT
GTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAA
CCATCTCCAAAGCCAAAGGGCAGCCCCGAGAACCACAGGTGTACACCCTG
CCCCCATCCCGGGAGGAGATGACCAAGAACCAGGTCAGCCTGACCTGCCT
GGTCAAAGGCTTCTATCCCAGCGACATCGCCGTGGAGTGGGAGAGCAATG
GGCAGCCGGAGAACAACTACAAGACCACGCCTCCCGTGCTGGACTCCGAC
GGCTCCTTCTTCCTCTATAGCAAGCTCACCGTGGACAAGAGCAGGTGGCA
GCAGGGGAACGTCTTCTCATGCTCCGTGATGCATGAGGCTCTGCACAACC
ACTACACGCAGAAGAGCCTCTCCCTGTCCCCGGGTAAA <SEQ ID NO: 8; PRT1; human>
EVQLVQSGGGLVKPGGSLRLSCAASGFTFSSYSMNWVRQAPGKGLEWVSS
ISSSSSYIYYADSVKGRFTISRDNAKNSLYLQMNSLRAEDTAVYYCARVT
DAFDIWGQGTMVTVSSASTKGPSVLPLAPSSKSTSGGTAALGCLVKDYFP
EPVTVSWNSGALTSGVHTFPAVLQSSGLYSLSSVVTVPSSSLGTQTYICN
VNHKPSNTKVDKRVEPKSCDKTHTCPPCPAPELLGGPSVFLFPPKPKDTL
MISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK

SEQUENCE LISTING

<SEQ ID NO: 9; PRT1; human>
```
                      A SVGLPSVSLD LPRLSIQKDI LTIKANTTLQ ITCRGQRDLD
WLWPNNQSGS EQRVEVTECS DGLFCKTLTI PKVIGNDTGA YKCFYRETDL ASVIYVYVQD
YRSPFIASVS DQHGVVYITE NKNKTVVIPC LGSISNLNVS LCARYPEKRF VPDGNRISWD
SKKGFTIPSY MISYAGMVFC EAKINDESYQ SIMYIVVVG  YRIYDVVLSP SHGIELSVGE
KLVLNCTART ELNVGIDFNW EYPSSKHQHK KLVNRDLKTQ SGSEMKKFLS TLTIDGVTRS
DQGLYTCAAS SGLMTKKNST FVRVHEKPFV AFGSGMESLV EATVGERVRI PAKYLGYPPP
EIKWYKNGIP LESNHTIKAG HVLTIMEVSE RDTGNYTVIL INPISKEKQS HVVSLVVYVP
PQIGEKSLIS PVDSYQYGIT QTLTCTVYAI PPPHHIHWYW QLEEECANEP SQAVSVINPY
PCEEWRSVED FQGGNKIEVN KNQFALIEGK NKTVSTLVIQ AANVSALYKC EAVNKVGRGE
RVISPHVTRG PEITLQPDMQ PTEQESVSLW CTADRSTFEN LIWYKLGPQP LPIHVGELPT
PVCKNLDTLW KLNATMFSNS TNDILIMELK NASLQDQGDY VCLAQDRKTK KRHCVVRQLT
VLERVAPTIT GNLENQTTSI GESIEVSCTA SGNPPPQIMW FKDNETLVED SGIVLKDGNR
NLTIRRVRKE DEGLYTCQAC SVLGCAKVEA FFIIEGAQEK TNLEIIILVG TAVIAMFFWL
LLVIILRTVK RANGGELKTG YLSIVMDPDE LPLDEHCERL PYDASKWEFP RDRLKLGKPL
GRGAFGQVIE ADAFGIDKTA TCRTVAVKML KEGATHSEHR ALMSELKILI HIGHHLNVVN
LLGACTKPGG PLMVIVEFCK FGNLSTYLRS KRNEFVPYKT KGARFRQGKD YVGAIPVDLK
RRLDSITSSQ SSASSGFVEE KSLSDVEEEE APEDLYKDFL TLEHLICYSF QVAKGMEFLA
SRKCIHRDLA ARNILLSEKN VVKICDFGLA RDIYKDPDYV RKGDARLPLK WMAPETIFDR
VYTIQSDVWS FGVLLWEIFS LGASPYPGVK IDEEFCRRLK EGIRMRAPDY TTPEMYQTML
DCWHGEPSQR PIFSELVEHL GNLLQANAQQ DGKDYIVLPI SETLSMEEDS GLSLPTSPVS
CMEEEEVCDP KFHYDNTAGI SQYLQNSKRK SRPVSVKIFE DIPLEEPEVK VIPDDNQTDS
GMVLASEELK TLEDRIKLSP SFGGMVPSKS RESVASEGSN QTSGYQSGYH SDDTDTTVYS
SEEAELLKLI EIGVQTGSTA QILQPDSGTT LSSPPV
```

I claim:

1. A method of treating non-small cell lung cancer in a human patient, comprising administering to a non-small cell lung cancer human patient in need of such treatment 300 or 400 mg daily of a compound of the formula:

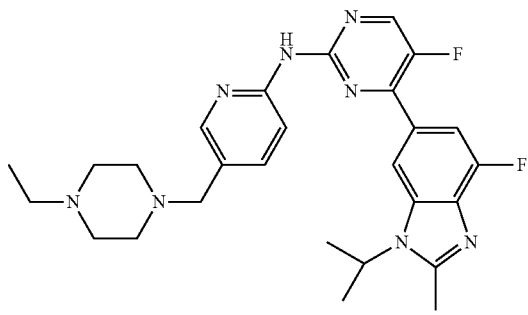 [SMILES: CCN1CCN(Cc2ccc(Nc3ncc(F)c(-c4cc(F)c5nc(C)n(C(C)C)c5c4)n3)nc2)CC1]

or a pharmaceutically acceptable salt thereof, in combination with 10 mg/kg once every three weeks of ramucirumab.

2. The method of claim 1, wherein the compound is

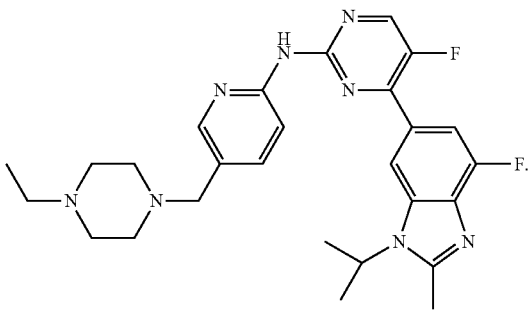 [SMILES: CCN1CCN(Cc2ccc(Nc3ncc(F)c(-c4cc(F)c5nc(C)n(C(C)C)c5c4)n3)nc2)CC1]

3. The method of claim 1 wherein the compound or salt thereof is administered orally and ramucirumab is administered intravenously.

4. A method of treating non-small cell lung cancer in a human patient, comprising administering to a non-small cell lung cancer human patient in need of such treatment 300 or 400 mg daily of a compound of the formula:

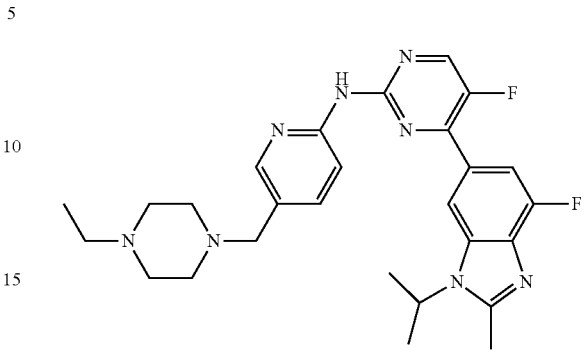

or a pharmaceutically acceptable salt thereof, in combination with 10 mg/kg of ramucirumab on the first day of a 21-day cycle.

5. The method of claim 4, wherein the compound is

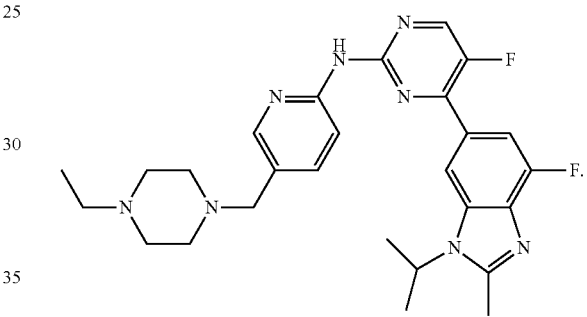

6. The method of claim 4 wherein the compound or salt thereof is administered orally and ramucirumab is administered intravenously.

* * * * *

SEQUENCE LISTING

<160> NUMBER OF SEQ ID NOS: 9

<210> SEQ ID NO 1
<211> LENGTH: 321
<212> TYPE: DNA
<213> ORGANISM: Homo sapiens

<400> SEQUENCE: 1

```
gacatccaga tgacccagtc tccatcttcc gtgtctgcat ctataggaga cagagtcacc    60
atcacttgtc gggcgagtca gggtattgac aactggttag ctggtatca  gcagaaacct   120
gggaaagccc ctaaactcct gatctacgat gcatccaatt tggacacagg ggtcccatca   180
aggttcagtg gaagtggatc tggaacatat tttactctca ccatcagtag cctgcaagct   240
gaagattttg cagtttattt ctgtcaacag gctaaagctt ttcctcccac tttcggcgga   300
gggaccaagg tggacatcaa a                                             321
```

<210> SEQ ID NO 2
<211> LENGTH: 107
<212> TYPE: PRT
<213> ORGANISM: Homo sapiens

<400> SEQUENCE: 2

```
Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Asp Asn Trp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Asp Thr Gly Val Pro Ser Arg Phe Ser Gly
    50                  55                  60

Ser Gly Ser Gly Thr Tyr Phe Thr Leu Thr Ile Ser Ser Leu Gln Ala
65                  70                  75                  80

Glu Asp Phe Ala Val Tyr Phe Cys Gln Gln Ala Lys Ala Phe Pro Pro
```

```
                      85                  90                  95
Thr Phe Gly Gly Gly Thr Lys Val Asp Ile Lys
                100                 105

<210> SEQ ID NO 3
<211> LENGTH: 348
<212> TYPE: DNA
<213> ORGANISM: Homo sapiens

<400> SEQUENCE: 3
gaggtccagc tggtgcagtc tgggggaggc ctggtcaagc ctgggggtc cctgagactc      60 tcctgtgcag cctctggatt caccttcagt agctatagca tgaactgggt ccgccaggct    120
ccagggaagg gctggagtg gtctcatcc attagtagta gtagtagtta catatactac      180
gcagactcag tgaagggccg attcaccatc tccagagaca cgccaagaa ctcactgtat     240 ctgcaaatga acagcctgag agccgaggac acggctgtgt attactgtgc gagagtcaca    300
gatgcttttg atatctgggg ccaagggaca atggtcaccg tctcaagc                348

<210> SEQ ID NO 4
<211> LENGTH: 116
<212> TYPE: PRT
<213> ORGANISM: Homo sapiens

<400> SEQUENCE: 4

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
            100                 105                 110

Thr Val Ser Ser
        115

<210> SEQ ID NO 5
<211> LENGTH: 642
<212> TYPE: DNA
<213> ORGANISM: Homo sapiens

<400> SEQUENCE: 5
gacatccaga tgacccagtc tccatcttcc gtgtctgcat ctataggaga cagagtcacc    60
atcacttgtc gggcgagtca gggtattgac aactggttag ctggtatca gcagaaacct    120 gggaaagccc ctaaactcct gatctacgat gcatccaatt tggacacagg gtcccatca    180 aggttcagtg gaagtggatc tgggacatat tttactctca ccatcagtag cctgcaagct    240 gaagatttg cagtttattt ctgtcaacag gctaaagctt ttcctcccac tttcggcgga    300
gggaccaagg tggacatcaa acgaactgtg gctgcaccat ctgtcttcat cttcccgcca    360
tctgatgagc agttgaaatc tggaactgcc tctgttgtgt gcctgctgaa taacttctat    420
```

```
cccagagagg ccaaagtaca gtggaaggtg ataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                         642
```

```
<210> SEQ ID NO 6
<211> LENGTH: 214
<212> TYPE: PRT
<213> ORGANISM: Homo sapiens

<400> SEQUENCE: 6

Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Asp Asn Trp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Asp Thr Gly Val Pro Ser Arg Phe Ser Gly
    50                  55                  60

Ser Gly Ser Gly Thr Tyr Phe Thr Leu Thr Ile Ser Ser Leu Gln Ala
65                  70                  75                  80

Glu Asp Phe Ala Val Tyr Phe Cys Gln Gln Ala Lys Ala Phe Pro Pro
                85                  90                  95

Thr Phe Gly Gly Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 7
<211> LENGTH: 1338
<212> TYPE: DNA
<213> ORGANISM: Homo sapiens

<400> SEQUENCE: 7
gaggtccagc tggtgcagtc tgggggaggc ctggtcaagc ctggggggtc cctgagactc       60
tcctgtgcag cctctggatt caccttcagt agctatagca tgaactgggt ccgccaggct      120
ccagggaagg gctggagtg gtctcatcc attagtagta gtagtagtta catatactac       180
gcagactcag tgaagggccg attcaccatc tccagagaca acgccaagaa ctcactgtat      240
ctgcaaatga acagcctgag agccgaggac acggctgtgt attactgtgc gagagtcaca      300
gatgcttttg atatctgggg ccaagggaca atggtcaccg tctcaagcgc tagcaccaag      360
ggcccatcgg tcttccccct ggcaccctcc tccaagagca cctctggggg cacagcggcc      420
```

-continued

```
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagagag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cccccatccc gggaggagat gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctatag caagctcacc gtggacaaga gcaggtggca gcaggggaac   1260
gtcttctcat gctccgtgat gcatgaggct ctgcacaacc actacacgca gaagagcctc   1320
tccctgtccc cgggtaaa                                                 1338
```

<210> SEQ ID NO 8
<211> LENGTH: 446
<212> TYPE: PRT
<213> ORGANISM: Homo sapiens

<400> SEQUENCE: 8

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
            100                 105                 110

Thr Val Ser Ser Ala Ser Thr Lys Gly Pro Ser Val Leu Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

-continued

Lys Val Asp Lys Arg Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 9
<211> LENGTH: 1337
<212> TYPE: PRT
<213> ORGANISM: Homo sapiens

<400> SEQUENCE: 9

Ala Ser Val Gly Leu Pro Ser Val Ser Leu Asp Leu Pro Arg Leu Ser
1               5                   10                  15

Ile Gln Lys Asp Ile Leu Thr Ile Lys Ala Asn Thr Thr Leu Gln Ile
            20                  25                  30

Thr Cys Arg Gly Gln Arg Asp Leu Asp Trp Leu Trp Pro Asn Asn Gln
            35                  40                  45

Ser Gly Ser Glu Gln Arg Val Glu Val Thr Glu Cys Ser Asp Gly Leu
50                  55                  60

Phe Cys Lys Thr Leu Thr Ile Pro Lys Val Ile Gly Asn Asp Thr Gly
65                  70                  75                  80

Ala Tyr Lys Cys Phe Tyr Arg Glu Thr Asp Leu Ala Ser Val Ile Tyr
            85                  90                  95

Val Tyr Val Gln Asp Tyr Arg Ser Pro Phe Ile Ala Ser Val Ser Asp
            100                 105                 110

Gln His Gly Val Val Tyr Ile Thr Glu Asn Lys Asn Lys Thr Val Val
            115                 120                 125

Ile Pro Cys Leu Gly Ser Ile Ser Asn Leu Asn Val Ser Leu Cys Ala

-continued

```
                130                 135                 140
Arg Tyr Pro Glu Lys Arg Phe Val Pro Asp Gly Asn Arg Ile Ser Trp
145                 150                 155                 160

Asp Ser Lys Lys Gly Phe Thr Ile Pro Ser Tyr Met Ile Ser Tyr Ala
                165                 170                 175

Gly Met Val Phe Cys Glu Ala Lys Ile Asn Asp Glu Ser Tyr Gln Ser
                180                 185                 190

Ile Met Tyr Ile Val Val Val Gly Tyr Arg Ile Tyr Asp Val Val
                195                 200                 205

Leu Ser Pro Ser His Gly Ile Glu Leu Ser Val Gly Glu Lys Leu Val
                210                 215                 220

Leu Asn Cys Thr Ala Arg Thr Glu Leu Asn Val Gly Ile Asp Phe Asn
225                 230                 235                 240

Trp Glu Tyr Pro Ser Ser Lys His Gln His Lys Lys Leu Val Asn Arg
                245                 250                 255

Asp Leu Lys Thr Gln Ser Gly Ser Glu Met Lys Lys Phe Leu Ser Thr
                260                 265                 270

Leu Thr Ile Asp Gly Val Thr Arg Ser Asp Gln Gly Leu Tyr Thr Cys
                275                 280                 285

Ala Ala Ser Ser Gly Leu Met Thr Lys Lys Asn Ser Thr Phe Val Arg
290                 295                 300

Val His Glu Lys Pro Phe Val Ala Phe Gly Ser Gly Met Glu Ser Leu
305                 310                 315                 320

Val Glu Ala Thr Val Gly Glu Arg Val Arg Ile Pro Ala Lys Tyr Leu
                325                 330                 335

Gly Tyr Pro Pro Glu Ile Lys Trp Tyr Lys Asn Gly Ile Pro Leu
                340                 345                 350

Glu Ser Asn His Thr Ile Lys Ala Gly His Val Leu Thr Ile Met Glu
                355                 360                 365

Val Ser Glu Arg Asp Thr Gly Asn Tyr Thr Val Ile Leu Thr Asn Pro
                370                 375                 380

Ile Ser Lys Glu Lys Gln Ser His Val Val Ser Leu Val Val Tyr Val
385                 390                 395                 400

Pro Pro Gln Ile Gly Glu Lys Ser Leu Ile Ser Pro Val Asp Ser Tyr
                405                 410                 415

Gln Tyr Gly Thr Thr Gln Thr Leu Thr Cys Thr Val Tyr Ala Ile Pro
                420                 425                 430

Pro Pro His His Ile His Trp Tyr Trp Gln Leu Glu Glu Glu Cys Ala
                435                 440                 445

Asn Glu Pro Ser Gln Ala Val Ser Val Thr Asn Pro Tyr Pro Cys Glu
                450                 455                 460

Glu Trp Arg Ser Val Glu Asp Phe Gln Gly Asn Lys Ile Glu Val
465                 470                 475                 480

Asn Lys Asn Gln Phe Ala Leu Ile Glu Gly Lys Asn Lys Thr Val Ser
                485                 490                 495

Thr Leu Val Ile Gln Ala Ala Asn Val Ser Ala Leu Tyr Lys Cys Glu
                500                 505                 510

Ala Val Asn Lys Val Gly Arg Gly Glu Arg Val Ile Ser Phe His Val
                515                 520                 525

Thr Arg Gly Pro Glu Ile Thr Leu Gln Pro Asp Met Gln Pro Thr Glu
530                 535                 540

Gln Glu Ser Val Ser Leu Trp Cys Thr Ala Asp Arg Ser Thr Phe Glu
545                 550                 555                 560
```

-continued

Asn Leu Thr Trp Tyr Lys Leu Gly Pro Gln Pro Leu Pro Ile His Val
                565                 570                 575

Gly Glu Leu Pro Thr Pro Val Cys Lys Asn Leu Asp Thr Leu Trp Lys
            580                 585                 590

Leu Asn Ala Thr Met Phe Ser Asn Ser Thr Asn Asp Ile Leu Ile Met
        595                 600                 605

Glu Leu Lys Asn Ala Ser Leu Gln Asp Gln Gly Asp Tyr Val Cys Leu
    610                 615                 620

Ala Gln Asp Arg Lys Thr Lys Arg His Cys Val Val Arg Gln Leu
625                 630                 635                 640

Thr Val Leu Glu Arg Val Ala Pro Thr Ile Thr Gly Asn Leu Glu Asn
                645                 650                 655

Gln Thr Thr Ser Ile Gly Glu Ser Ile Glu Val Ser Cys Thr Ala Ser
            660                 665                 670

Gly Asn Pro Pro Pro Gln Ile Met Trp Phe Lys Asp Asn Glu Thr Leu
        675                 680                 685

Val Glu Asp Ser Gly Ile Val Leu Lys Asp Gly Asn Arg Asn Leu Thr
    690                 695                 700

Ile Arg Arg Val Arg Lys Glu Asp Glu Gly Leu Tyr Thr Cys Gln Ala
705                 710                 715                 720

Cys Ser Val Leu Gly Cys Ala Lys Val Glu Ala Phe Phe Ile Ile Glu
                725                 730                 735

Gly Ala Gln Glu Lys Thr Asn Leu Glu Ile Ile Ile Leu Val Gly Thr
            740                 745                 750

Ala Val Ile Ala Met Phe Phe Trp Leu Leu Leu Val Ile Ile Leu Arg
        755                 760                 765

Thr Val Lys Arg Ala Asn Gly Gly Glu Leu Lys Thr Gly Tyr Leu Ser
    770                 775                 780

Ile Val Met Asp Pro Asp Glu Leu Pro Leu Asp Glu His Cys Glu Arg
785                 790                 795                 800

Leu Pro Tyr Asp Ala Ser Lys Trp Glu Phe Pro Arg Asp Arg Leu Lys
                805                 810                 815

Leu Gly Lys Pro Leu Gly Arg Gly Ala Phe Gly Gln Val Ile Glu Ala
            820                 825                 830

Asp Ala Phe Gly Ile Asp Lys Thr Ala Thr Cys Arg Thr Val Ala Val
        835                 840                 845

Lys Met Leu Lys Glu Gly Ala Thr His Ser Glu His Arg Ala Leu Met
    850                 855                 860

Ser Glu Leu Lys Ile Leu Ile His Ile Gly His His Leu Asn Val Val
865                 870                 875                 880

Asn Leu Leu Gly Ala Cys Thr Lys Pro Gly Gly Pro Leu Met Val Ile
                885                 890                 895

Val Glu Phe Cys Lys Phe Gly Asn Leu Ser Thr Tyr Leu Arg Ser Lys
            900                 905                 910

Arg Asn Glu Phe Val Pro Tyr Lys Thr Lys Gly Ala Arg Phe Arg Gln
        915                 920                 925

Gly Lys Asp Tyr Val Gly Ala Ile Pro Val Asp Leu Lys Arg Arg Leu
    930                 935                 940

Asp Ser Ile Thr Ser Ser Gln Ser Ser Ala Ser Ser Gly Phe Val Glu
945                 950                 955                 960

Glu Lys Ser Leu Ser Asp Val Glu Glu Glu Ala Pro Glu Asp Leu
                965                 970                 975

-continued

```
Tyr Lys Asp Phe Leu Thr Leu Glu His Leu Ile Cys Tyr Ser Phe Gln
        980                 985                 990

Val Ala Lys Gly Met Glu Phe Leu Ala Ser Arg Lys Cys Ile His Arg
        995                 1000                1005

Asp Leu Ala Ala Arg Asn Ile Leu Leu Ser Glu Lys Asn Val Val
        1010                1015            1020

Lys Ile Cys Asp Phe Gly Leu Ala Arg Asp Ile Tyr Lys Asp Pro
        1025                1030            1035

Asp Tyr Val Arg Lys Gly Asp Ala Arg Leu Pro Leu Lys Trp Met
        1040                1045            1050

Ala Pro Glu Thr Ile Phe Asp Arg Val Tyr Thr Ile Gln Ser Asp
        1055                1060            1065

Val Trp Ser Phe Gly Val Leu Leu Trp Glu Ile Phe Ser Leu Gly
        1070                1075            1080

Ala Ser Pro Tyr Pro Gly Val Lys Ile Asp Glu Glu Phe Cys Arg
        1085                1090            1095

Arg Leu Lys Glu Gly Thr Arg Met Arg Ala Pro Asp Tyr Thr Thr
        1100                1105            1110

Pro Glu Met Tyr Gln Thr Met Leu Asp Cys Trp His Gly Glu Pro
        1115                1120            1125

Ser Gln Arg Pro Thr Phe Ser Glu Leu Val Glu His Leu Gly Asn
        1130                1135            1140

Leu Leu Gln Ala Asn Ala Gln Gln Asp Gly Lys Asp Tyr Ile Val
        1145                1150            1155

Leu Pro Ile Ser Glu Thr Leu Ser Met Glu Glu Asp Ser Gly Leu
        1160                1165            1170

Ser Leu Pro Thr Ser Pro Val Ser Cys Met Glu Glu Glu Glu Val
        1175                1180            1185

Cys Asp Pro Lys Phe His Tyr Asp Asn Thr Ala Gly Ile Ser Gln
        1190                1195            1200

Tyr Leu Gln Asn Ser Lys Arg Lys Ser Arg Pro Val Ser Val Lys
        1205                1210            1215

Thr Phe Glu Asp Ile Pro Leu Glu Glu Pro Glu Val Lys Val Ile
        1220                1225            1230

Pro Asp Asp Asn Gln Thr Asp Ser Gly Met Val Leu Ala Ser Glu
        1235                1240            1245

Glu Leu Lys Thr Leu Glu Asp Arg Thr Lys Leu Ser Pro Ser Phe
        1250                1255            1260

Gly Gly Met Val Pro Ser Lys Ser Arg Glu Ser Val Ala Ser Glu
        1265                1270            1275

Gly Ser Asn Gln Thr Ser Gly Tyr Gln Ser Gly Tyr His Ser Asp
        1280                1285            1290

Asp Thr Asp Thr Thr Val Tyr Ser Ser Glu Glu Ala Glu Leu Leu
        1295                1300            1305

Lys Leu Ile Glu Ile Gly Val Gln Thr Gly Ser Thr Ala Gln Ile
        1310                1315            1320

Leu Gln Pro Asp Ser Gly Thr Thr Leu Ser Ser Pro Pro Val
        1325                1330            1335
```